(12) United States Patent
Feng et al.

(10) Patent No.: US 10,947,637 B2
(45) Date of Patent: Mar. 16, 2021

(54) NANOPORE FORMING METHOD AND USES THEREOF

(71) Applicants: Ecole Polytechnique Federale De Lausanne (EPFL), Lausanne (CH); Roche Sequencing Solutions, Inc., Pleasanton, CA (US)

(72) Inventors: Jiandong Feng, Morges (CH); Ke Liu, Chavannes-pres-Renens (CH); Aleksandra Radenovic, St. Sulpice (CH); Yann Astier, Livermore, CA (US)

(73) Assignees: Ecole Polytechnique Federale De Lausanne (EPFL), Lausanne (CH); Roche Sequencing Solutions, Inc., Pleasanton, CA (US)

( * ) Notice: Subject to any disclaimer, the term of this patent is extended or adjusted under 35 U.S.C. 154(b) by 8 days.

(21) Appl. No.: 16/432,163

(22) Filed: Jun. 5, 2019

(65) Prior Publication Data
US 2019/0323143 A1    Oct. 24, 2019

Related U.S. Application Data

(60) Division of application No. 15/688,264, filed on Aug. 28, 2017, now Pat. No. 10,364,507, which is a
(Continued)

(30) Foreign Application Priority Data

Mar. 12, 2015 (EP) .................................. 15158894
Jun. 8, 2015 (EP) .................................. 15171077

(51) Int. Cl.
*C25F 3/12* (2006.01)
*B23H 9/14* (2006.01)
(Continued)

(52) U.S. Cl.
CPC ................. *C25F 3/12* (2013.01); *B23H 7/20* (2013.01); *B23H 9/14* (2013.01); *C12Q 1/6869* (2013.01);
(Continued)

(58) Field of Classification Search
CPC ........................................................ C25F 3/12
See application file for complete search history.

(56) References Cited

U.S. PATENT DOCUMENTS 9,656,293 B2 * 5/2017 Kuan ................. B01D 67/0062
9,777,390 B2 * 10/2017 Godin ................ B81C 1/00087
2015/0108008 A1    4/2015 Kwok et al.

FOREIGN PATENT DOCUMENTS

WO    2013/167952 A1    11/2013
WO    2014/144818 A2    9/2014
WO    2015/121394 A1    8/2015

OTHER PUBLICATIONS

International Search Report and Written Opinion dated Sep. 15, 2016 in PCT Appln. PCT/IB2016/051425; 12 pages.
(Continued)

*Primary Examiner* — Brian W Cohen
(74) *Attorney, Agent, or Firm* — Kilpatrick Townsend and Stockton LLP

(57) ABSTRACT

The invention relates to a method for making nanopores in thin layers or monolayers of transition metal dichalcogenides that enables accurate and controllable formation of pore within those thin layer(s) with sub-nanometer precision.

16 Claims, 14 Drawing Sheets

Related U.S. Application Data continuation of application No. PCT/IB2016/051425, filed on Mar. 12, 2016.

(60) Provisional application No. 62/286,235, filed on Jan. 22, 2016.

(51) Int. Cl.

| | | |
|---|---|---|
| B23H 7/20 | (2006.01) | |
| G01N 33/487 | (2006.01) | |
| G01N 27/414 | (2006.01) | |
| C12Q 1/6869 | (2018.01) | |
| C25F 7/00 | (2006.01) | |
| G01N 27/447 | (2006.01) | |
| G01R 19/00 | (2006.01) | |

(52) U.S. Cl.
CPC ........... *C25F 7/00* (2013.01); *G01N 27/4145* (2013.01); *G01N 27/44791* (2013.01); *G01N 33/48721* (2013.01); *G01R 19/0092* (2013.01)

(56) References Cited

OTHER PUBLICATIONS

Bonde et al., 2008, Faraday Discussions, vol. 140, 219-231.
Branton D. et al.; "The potential and challenges of nanopore sequencing"; Nature Biotechnology; vol. 26; Oct. 9, 2008; pp. 1146-1153.
Briggs K. et al.; "Kinetics of nanopore fabrication during controlled breakdown of dielectric membranes in solution"; Nanotechnology; vol. 26, No. 8; Feb. 4, 2015.
Chung Sh et al.; "Forward-backward non-linear filtering technique for extracting small biological signals from noise"; J. Neurosci. Methods; vol. 40, No. 1; Nov. 1991; pp. 71-86.
Cohen-Tanugi D et al.; "Water desalination across nanoporous graphene"; Nano Letters; vol. 12, No. 7; Jul. 11, 2012; pp. 3602-3608.
Dekker, C.; "Solid-state nanopores"; Nature Nanotechnology; vol. 2; Mar. 4, 2007; pp. 209-215.
Dumcenco et al.; "Large-area Epitaxial Monolayer MoS2"; ACS Nano; vol. 9; 2015; p. 4611.
Feng et al., Nature Nanotechnology; vol. 10, 2015; p. 1070.
Fischbein M. et al.; "Electron beam nanosculpting of suspended graphene sheets"; Applied Physics Letters; vol. 93, Issue 11; No. 113107; 2008: doi:http://dx.doi.org/10.1063/1.2980518.
Garaj S. et al.; "Graphene as a subnanometre trans-electrode membrane"; Nature; vol. 467; Sep. 9, 2010; pp. 190-193.
Kotulska, M. et al.; "Metastable Pores at the Onset of Constant-Current Electroporation"; J. Membrane Biology; vol. 236; 2010; pp. 37-41.
Kowalczyk S. et al.; "Modeling the Conductance and DNA Blockade of Solid-State Nanopores"; Nanotechnology; vol. 22; 2011; pp. 1-5.
Kwok H. et al; "Nanopore Fabrication by Controlled Dielectric Breakdown"; PLOS ONE; vol. 9, No. 3' Mar. 21, 2014; 6 pages.
Liu K. et al; "Atomically Thin Molybdenum Disulfide Nanopores with High Sensitivity for DNA Translocation"; ACS NANO; vol. 8, No. 3; Mar. 25, 2014; pp. 2504-2511.
Liu K. et al.; "Growth of Large-Area and Highly Crystalline MoS2 Thin Layers on Insulating Substrates"; Nano Lett.; vol. 12, No. 3; Feb. 27, 2012; pp. 1538-1544.
Liu T. et al.; "A light-induced spin crossover actuated single-chain magnet"; Nature Communications; vol. 4; Nov. 20, 2013; doi:10.1038/ncomms3826.
Nicolosi V. et al.; "Liquid Exfoliation of layered Materials"; Science, vol. 340; Jun. 21, 2013; pp. 1226419-1-1226419-18.
Novoselov K. et al., "Two-dimensional atomic crystals"; PNAS; vol. 102, No. 30; Jul. 26, 2005; pp. 10451-10453.
Park S. et al.; "Fabrication of Nanopores in Silicon Chips Using Feedback Chemical Etching"; Small; vol. 3, 2007; pp. 116-119.
Raillon C. et al.; "Fast and automatic processing of multi-level events in nanopore translocation experiments"; Nanoscale; vol. 4; 2012; pp. 4916-4924.
Rao C.N.R. et al; "Graphene Analogues of Inorganic Layered Materials"; Angewandte Chemie International Edition; vol. 52, No. 50; Oct. 11, 2013; pp. 13162-13185.
Siwy Z. et al.; "Fabrication of a Synthetic Nanopore Ion Pump"; Physical Review Letters; vol. 89; Oct. 18, 2002; pp. 198103.
Yanagi I. et al; "Fabricating nanopores with diameters of sub-1 nm to 3 nm using multilevel pulse-voltage injection"; Scientific Reports; vol. 4; May 21, 2014; 7 pages.
Yuan W. et al.; "Nanoporous graphene materials"; Materials Today; vol. 17, Issue 2; Mar. 2014; pp. 77-85.

\* cited by examiner

| Temp [eV] | lifetime [s] | r [nm] | A [nm] | l [nm] | Δr | Δl | neutral groups cleaved | | | |
|---|---|---|---|---|---|---|---|---|---|---|
| 0.926 | 0.1 | 0.36 | 0.10 | 1.16 | 0.100 | 1.16 | 1 | | MoS₂ | | 1 |
| 0.5556 | 0.2 | 0.47 | 0.18 | 2.04 | 0.076 | 0.88 | 1 | | MoS₂ | | 2 |
| 0.4939 | 1.7 | 0.57 | 0.25 | 2.92 | 0.076 | 0.88 | 1 | | MoS₂ | | 3 |
| 0.6025 | 1.0 | 0.71 | 0.39 | 4.53 | 0.139 | 1.60 | 1 2/3 | | MoS₂ | MoS | 4 |
| 0.4939 | 0.1 | 0.79 | 0.49 | 5.82 | 0.094 | 1.09 | 1 | | MoS₂ | | 5 |
| 0.5556 | 2.7 | 0.87 | 0.60 | 6.93 | 0.114 | 1.31 | 1 1/3 | | MoS₂ | S₂ | 6 |
| 0.5556 | 0.8 | 0.96 | 0.72 | 8.34 | 0.122 | 1.41 | 1 1/3 | | MoS₂ | S₂ | 7 |
| 0.6025 | 3.2 | 1.08 | 0.91 | 10.53 | 0.189 | 2.19 | 2 | MoS₂ | MoS₂ | | 8 |
| 0.4322 | 1.5 | 1.14 | 1.02 | 11.79 | 0.109 | 1.26 | 1 1/3 | | MoS₂ | S₂ | 9 |
| 0.3087 | 0.1 | 1.18 | 1.10 | 12.72 | 0.080 | 0.93 | 1 | | MoS₂ | | 10 |
| 0.3087 | 0.1 | 1.23 | 1.18 | 13.67 | 0.083 | 0.96 | 1 | | MoS₂ | | 11 |
| 0.3087 | 1.1 | 1.27 | 1.27 | 14.66 | 0.085 | 0.98 | 1 | | MoS₂ | | 12 |
| 0.6791 | 1.8 | 1.36 | 1.46 | 16.92 | 0.196 | 2.26 | 2 1/3 | MoS₂ | MoS₂ | S₂ | 13 |
| 0.4939 | 0.7 | 1.43 | 1.61 | 18.54 | 0.149 | 1.72 | 1 2/3 | | MoS₂ | Mo | 14 |
| 0.7409 | 2.7 | 1.53 | 1.84 | 21.35 | 0.234 | 2.71 | 2 2/3 | MoS₂ | MoS₂ | Mo | 15 |
| 0.6791 | 0.4 | 1.62 | 2.07 | 23.96 | 0.226 | 2.62 | 2 2/3 | MoS₂ | MoS₂ | Mo | 16 |
| 0.6173 | 1.4 | 1.71 | 2.29 | 26.45 | 0.215 | 2.49 | 2 2/3 | MoS₂ | MoS₂ | Mo | 17 |
| 0.7409 | 0.1 | 1.80 | 2.55 | 29.57 | 0.270 | 3.12 | 3 | MoS₂ | MoS₂ | MoS₂ | 18 |
| 0.3087 | 0.1 | 1.84 | 2.67 | 30.91 | 0.116 | 1.34 | 1 1/3 | | MoS₂ | S₂ | 19 |
| 0.4321 | 0.1 | 1.90 | 2.84 | 32.84 | 0.166 | 1.92 | 2 | MoS₂ | MoS₂ | | 20 |
| 0.2469 | 0.5 | 1.93 | 2.93 | 33.96 | 0.097 | 1.12 | 1 | | MoS₂ | | 21 |
| mean | diameter | | | | | | | | | | |
| | | 1.9 nm | 2.9 | 34.0 | | 34 | | | | | |

*FIG. 5E*

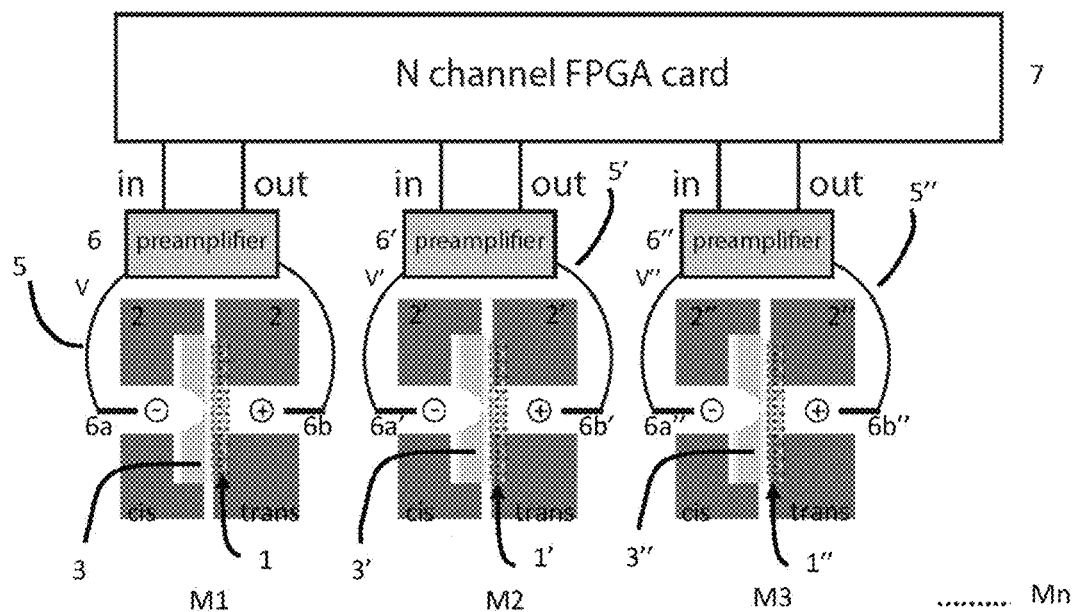
*FIG. 8*
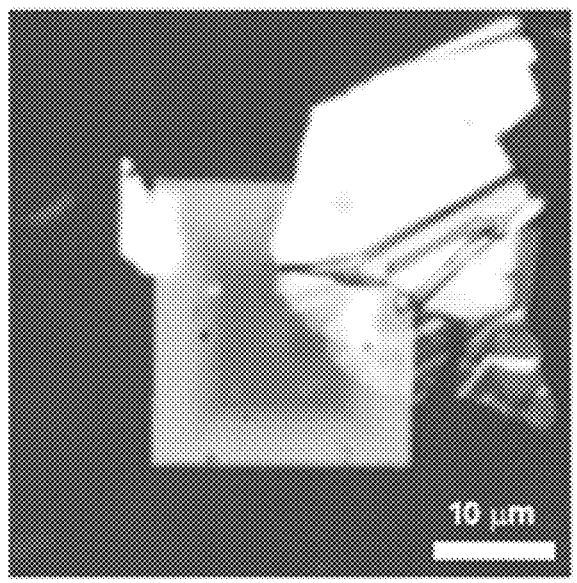
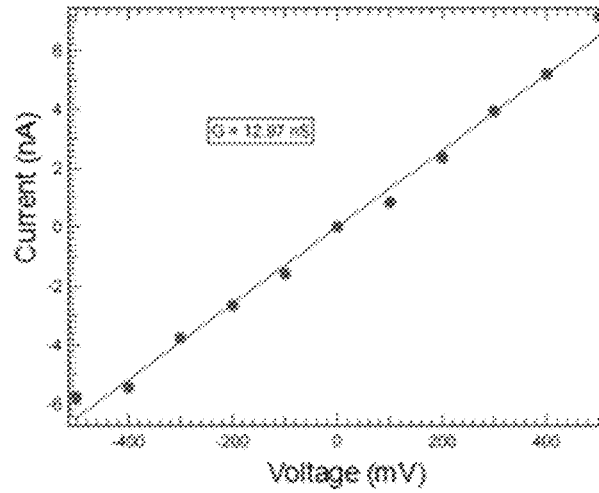
*FIG. 9A*              *FIG. 9B*

NANOPORE FORMING METHOD AND USES THEREOF

CROSS-REFERENCE TO RELATED APPLICATIONS

This application is a divisional of U.S. patent application Ser. No. 15/688,264 filed Aug. 28, 2017, which is a continuation of PCT Application No. PCT/IB2016/051425 filed Mar. 12, 2016, which claims the benefit of priority to European Patent Application No. 15158894.4, entitled "NANOPORE FORMING METHOD AND USES THEREOF," filed Mar. 12, 2015; European Patent Application No. 15171077.9, entitled "NANOPORE FORMING METHOD AND USES THEREOF," filed Jun. 8, 2015; and U.S. Provisional Patent Application No. 62/286,235, entitled "NOVEL METHOD FOR NANOPORE FORMATION IN ULTRATHIN MEMBRANES SUITABLE FOR MANUFACTURE," filed Jan. 22, 2016, the contents of all of which are incorporated herein by reference for all purposes.

FIELD OF THE INVENTION

The present invention pertains generally to the fields of nanopore forming in ultrathin membranes based on two-dimensional materials, in particular for use in molecular sensing devices, more particularly solid-state sensing of biomolecules such as DNA, RNA and proteins.

BACKGROUND OF THE INVENTION

Solid state nanopore bio-sensing is emerging as a rapid single molecule sensing technique (Branton et al., 2008, *Nature Biotechnology*, 26, 1146; Dekker, 2007, *Nature Nanotechnology* 2, 209). Conceptually, a single nanometer size aperture located on a membrane can detect electrophoretically driven biomolecules translocation in a high throughput manner, revealing localized information of the analyte. However, the formation of single nanopores relies heavily on expensive instrumentation, i.e., Transmission Electron Microscope (TEM) and well trained TEM user, which renders it still confined to laboratory use since this nanopore fabrication process is time-consuming, expensive, not scalable and hard to control at the nm scale.

Further, high costs of the TEM use, coupled with its high initial investment and the time consuming pore drilling process (1 hour machine and operator time per device) limit the more extensive application of solid state nanopores in the bio-sensing field. In addition, not all TEM drilled nanopores are hydrophilic and functional for the sensing of biomolecules. In addition, interaction with the high energy electron beam can cause damage especially when dealing with membranes in 2 D materials.

Many efforts, such as chemical wet-etching of silicon (Park et al., 2007, *Small* 3, 116-119) or polyethylene terephthalate film (Siwy et al., 2002, Physical review letters 89, 198103) have been carried out towards mass production of nanopores. Recently, a facile method has been reported using dielectric breakdown to make individual nanopores (3-30 nm diameter) on insulating silicon nitride membranes (5-30 nm thick) without the need of TEM_ENREF_8 (Kwok et al., 2014, *Plos One* 9, doi:10.1371/journal.pone.0092880, WO 2013/167952) for the in-situ forming of nanopores. However, those techniques based on dielectric breakdown need to apply high voltages pulses to the membranes which should be as short as possible for trying to monitor the nanopore diameter during its formation (WO 2014/144818).

When reaching dielectric breakdown, the process of pore forming becomes rather uncontrollable which is problematic for reproducibility and quality control of the nanopore size, especially when formed in-situ in a nanopore bio-sensing device, thereby leading to important production waste if the quality of the pore does not correspond in fine to the prescribed parameters.

Atomically thin nanopore membranes, graphene (Garaj et al., 2010, *Nature*, 467, 190) and molybdenum disulphide ($MoS_2$) (Feng et al., 2015, *Nature Nanotechnology*, 10, 1070) have drawn much attention recently due to their unprecedented single nucleotide resolution and holds promise as a candidate for so called $3^{rd}$ generation DNA sequencers. Therefore, if fabrication of nanostructures with sub-nanometer, or even single-atom precision has been a long-term goal for nanotechnology in general, there is now a raise of interest for those thin nanopore membranes and an increased need for cost-effective and reliable techniques for nanopore formation in those membranes.

In particular, since the differentiation of biomolecules relies strongly on the pore diameter, there is a high need for developing methods allowing controllable nanopore fabrication, which would enable mass production nanopore in 2D membranes such as $MoS_2$ even below 4 nm with atomic precision.

BRIEF SUMMARY OF THE INVENTION

An object of this invention is to provide a method for making nanopores in thin nanopore membranes of transition metal dichalcogenide that enables accurate and controllable formation of pore with sub-nanometer precision.

It is advantageous to provide a method of nanopore formation where the pore formation can be carried out in situ, notably in a nanopore bio-sensing device.

It is advantageous to provide a method of nanopore formation where the size of the pore is monitored during pore formation and adapted on demand, depending on the sizing need for the different applications such as the type of biomolecules to be sensed (e.g. proteins, or DNA-protein complexes, ss-DNA, dsDNA, RNA polymers, nucleotides, Nucleic Acid surrogates, or any non-natural polymers DNA tags).

It is advantageous to provide a system for nanopore formation that is economical to implement for mass production and easy to use.

It is advantageous to provide a system for nanopore formation that allows the formation of a broad series of nanopore in parallel on different membranes.

Another object of this invention is to provide method for forming a nanopore in an electrochemically etchable 2D material.

Disclosed herein, according to a first aspect of the invention, is a method for forming a nanopore in a membrane of transition metal dichalcogenide (TMDC) crystals comprising the steps of:

provide a TMDC thin layer having from about 0.3 nm to 2 nm thickness ($H_m$) immersed in an electrically conducting liquid;

applying a transmembrane voltage (V) at a value higher than the oxidation potential of the transition metal of the said TMDC to the said TMDC thin layer;

measuring the ionic current ($I_t$) in the said electrically conducting liquid;

turning off the transmembrane voltage once the measured ionic current ($I_t$) has reached a value ($I_p$) corresponding to the electrical conductance of a pore in the TMDC thin layer having a prescribed diameter ($d_p$).

The applied transmembrane voltage is preferably an essentially constant DC voltage applied between electrodes located on opposing sides of the TMDC thin layer.

In an embodiment, the transition metal dichalcogenide (TMDC) is of chemical formula is $MX_2$, where M is a transition metal atom and X is a chalcogen (S, Se, or Te).

In a particular embodiment, M is a transition metal atom selected from Ta, Nb, Mo, W, Ti and Re.

According to a particular embodiment, the TMDC is selected from $MoS_2$, $SnSe_2$, $WS_2$, $TaS_2$, $MoSe_2$, $WSe_2$, and $TaSe_2$.

According to another particular embodiment, the TMDC is selected from $NbS_2$, $NbSe_2$, $TiS_2$, $TiSe_2$, $ReS_2$ and $ReSe_2$ According to a particular embodiment, the TMDC is $MoS_2$.

According to another particular embodiment, the TMDC is $WSe_2$.

According to a particular aspect, the TMDC thin layer can be employed in single, double or multilayer form.

According to a further particular aspect, the TMDC thin layer may be a monolayer.

According to a particular embodiment, the TMDC thin layer is suspended in an electrically conducting liquid in such a way that a portion of the thin layer extends over a support layer and the other portion of the thin layer is in contact of a support layer.

In an embodiment of the invention, the material of the support layer may comprise $SiN_x$, glass, $Al_2O_3$ or $HfO_2$.

In another embodiment of the invention, the material of the support layer may comprise quartz, or $TiO_2$.

According to another further particular embodiment, the membrane of transition metal dichalcogenide (TMDC) crystals is a single-layer.

According to an advantageous embodiment, the TMDC layer comprises $MoS_2$ thin layers or is a $MoS_2$ monolayer.

According to an advantageous embodiment, the TMDC layer comprises CVD grown thin layers or is a CVD grown monolayer.

According to another further embodiment, the TMDC layer comprises MoCVD grown thin layers or a MoCVD grown monolayer.

In an embodiment of the invention, the electrically conducting liquid may advantageously comprise or consist in an aqueous liquid comprising an electrolyte.

In an embodiment of the invention, the electrically conducting liquid may be different from each side of the transition metal dichalcogenide membrane, in particular when the nanopore formation process is to be conducted in situ in a nanopore sensing device.

In an embodiment of the invention, the electrolyte may be potassium chloride (KCl).

In an embodiment of the invention, the electrically conducting liquid is an aqueous ionic solution (e.g. water and KCl or any inorganic salts such as LiCl, NaCl, $MgCl_2$, $CaCl_2$) etc).

In another embodiment, the transmembrane voltage is applied in a continuous manner.

In another embodiment, the transmembrane voltage is applied for a period of time necessary to reach an ionic current value which corresponds to the electrical conductance of a pore having a prescribed diameter (prescribed current/conductance).

In an embodiment of the invention, the ionic current can be measured in an ionic current circuit comprising a pair of electrodes (e.g. Ag/AgCl or Pt) coupled to the conducting liquid on opposite sides of the membrane.

In an embodiment, the ionic current circuit comprises means to measure the ionic current configured to provide a signal used in the measurement of the conductance through the nanopore.

According to a particular embodiment, the transmembrane voltage is switched off once the measured ionic current ($I_t$) has reached a value ($I_p$) corresponding to the electrical conductance of a pore in the TMDC thin layer having a prescribed diameter ($d_p$).

According to another embodiment, the turning off of the transmembrane voltage is achieved by an automatic switch which is activated through a feed-back control circuit when a prescribed current/conductance is reached.

According to a particular embodiment, the turning off of the transmembrane voltage is achieved by a decrease of the transmembrane voltage to a value (Vd), wherein the value (Vd) is 50% of the voltage at which electrochemical reaction occurs for a given pore and experimental condition or lower than 50%, wherein the decrease is initiated once the measured ionic current ($I_t$) has reached a value ($I_p$) corresponding to the electrical conductance of a pore in the TMDC thin layer having a prescribed diameter ($d_p$). Typically, the said transmembrane voltage is decreased to a value ($V_d$) from about 800 mV-2V to about 50%-90% lower than said oxidation potential.

According to another embodiment, the decrease of the transmembrane voltage is achieved by an automatic variator which is activated through a feed-back control circuit when a prescribed current/conductance is reached.

According to another embodiment, the oxidation potential of a transition metal dichalcogenide can be determined by cyclic voltametry. For example, a voltage of 800 mV is higher (typically between 800 mV and 1,000 mV such as about 800 mV and 900 mV) than the oxidation potential of $MoS_2$ being oxidized to $Mo^{(VI)}$ and allows starting the ECR process.

For example, in the case of the transition metal dichalcogenide being $WSe_2$, a voltage of 1V is higher (typically between 1'000 mV and 1'200 mV than oxidation potential of $WSe_2$ being oxidized to $W^{(III)}$ and allows starting the ECR process.

For another example, in the case of the transition metal dichalcogenide being $WSe_2$, a voltage of 1V is higher (typically between 1000 mV and 2000 mV than oxidation potential of $WSe_2$ being oxidized to $W^{(III)}$ and allows starting the ECR process.

According to a particular embodiment, once the ECR process starts, the transmembrane voltage is applied at a potential slightly lower than oxidation potential for the bulk material, for example about 5% lower the oxidation potential (e.g. about 5% (±1 or 2%) lower). This allows the manufacture of a single pore at a vacancy instead of making several pores outside such vacancy.

According to a particular embodiment, the transmembrane voltage is applied at a potential slightly higher than oxidation potential (e.g. about 5 to 10% higher) and once the ECR process starts, the transmembrane voltage is applied at a potential slightly lower than oxidation potential for the bulk material, for example about 5±1 or 2% lower the oxidation potential.

According to another embodiment, is provided a method of manufacturing a nanopore sensing device comprising a step of forming a nanopore according to the invention.

According to a further embodiment, is provided a method of manufacturing a nanopore sensing device according to the invention further comprising a step, once the nanopore is formed, of exchanging the electrically conducting liquid in the cis side of the transition metal dichalcogenide membrane by an electrically conducting liquid. According to a particular aspect, this electrically conducting liquid comprises a room temperature ionic liquid (RTIL) or an aqueous ionic solution such as water and KCl or any inorganic salts such as LiCl, NaCl, $MgCl_2$ or $CaCl_2$).

In a further embodiment of the invention, the room temperature ionic liquid (RTIL) is selected from an essentially pure RTIL, optionally mixed with an organic solvent, or a mixture of a water-miscible RTIL in water with a water content from about 5 to about 50 wt %.

According to an embodiment, is provided a method according to the invention, wherein more than one TMDC thin layers are provided and a transmembrane voltage is applied to each of the TMDC thin layers in parallel.

Disclosed herein, according to a first aspect of the invention, is a method for forming a nanopore in an electrochemically etchable 2D material comprising the steps of:

providing at least one thin layer of said electrochemically etchable 2D material having from about 0.3 nm to 5 nm thickness (Hm) suspended in an electrically conducting liquid;

applying a transmembrane voltage (V) at a value slightly higher than the oxidation potential of a transition metal of said at least one electrochemically etchable thin layer configured for an electrochemical atomic etching of said thin layer;

measuring the ionic current (Ii) in the said electrically conducting liquid;

turning off the transmembrane voltage once the ionic current (Ii) has reached a value (Ip) corresponding to the electrical conductance of a pore within the said TMDC thin layer having a prescribed diameter (dp).

In a further embodiment of the invention, the electrochemically etchable 2D material is a membrane of transition metal dichalcogenide (TMDC) crystals or any electrochemically etchable 2D material such as hBn silicene.

In another further embodiment of the invention, the electrochemically etchable 2D material has a thickness of about 0.3-1.5 nm thickness (Hm).

In another further embodiment of the invention, the electrochemically etchable 2D material is a material as described in Nicolosi et al., 2013, Science, 340 (6139), *DOI: 10.1126*.

In a further embodiment of the invention, the electrochemically etchable 2D material is a membrane of transition metal dichalcogenide (TMDC) crystals or any electrochemically etchable 2D material selected from a group comprising hBn silicene, transition metal trichalcogenides, metal halides, transition metal oxides and the like.

The above mentioned features may be combined in any appropriate manner.

An advantageous characteristic of the invention is to provide a method where the pore characteristics such as size, shape, and edge properties are fully controllable and reproducible.

An advantageous characteristic of the invention is to provide a method where the pore formation process lasts for few minutes of less.

An advantageous characteristic of the invention is to provide a method where the formation of the nanopore(s) in the transition metal dichalcogenide membrane is achieved by atomically controlled electrochemical etching of transition metal dichalcogenide thin layer, including monolayers with a sub-nanometer precision According to one aspect, the method of the invention allows in-situ preparation of nanopores in membranes of a transition metal dichalcogenide by electrochemical reaction (ECR), in particular in a nanopore sensing device.

An advantageous characteristic of the invention is to provide a method where pore dimensions may be adjusted to the needs, in particular to the biomolecule to sense in a nanopore sensing device.

A noticeable advantage for a nanopore fabrication method of the invention is that biomolecule translocations can be performed in situ directly after ECR and size-control allows on-demand adaptation of the pore size, allowing sizing for the different types of biomolecules, e.g. proteins or DNA-protein complexes etc. . . .

According to a further aspect, the method can be applied to a plurality of transition metal dichalcogenide membranes using a multiple channels feedback control unit for monitoring the ionic current through a plurality of transition metal dichalcogenide membranes.

Referring to FIG. 8, is illustrated a method for forming a nanopore in a transition metal dichalcogenide membrane according to the invention wherein the transition metal dichalcogenide membrane is in a form of a thin layer (or a monolayer) 1 having from about 0.3 nm to 4 nm thickness as depicted in FIG. 1A wherein more than one TMDC thin layers (1, 1' and 1") are provided and a transmembrane voltage is applied to each of the TMDC thin layers in parallel (V, V' and V"). Each TMDC thin layer is suspended in an electrically conducting liquid (2, 2', 2") and each transmembrane voltage is applied at a value higher than the oxidation potential of the transition metal of the corresponding TMDC, measuring the ionic current ($I_i$) in the said electrically conducting liquid until the ionic current ($I_i$) has reached a value ($I_p$) corresponding to the electrical conductance of a pore within the metal dichalcogenide membrane having a prescribed diameter ($D_p$).

The TMDC thin layer 1 is configured such that the portion of the TMDC thin layer where the formation of a nanopore will be carried out is suspended in an electrically conducting liquid and the other portion of the TMDC thin layer is supported by a support layer (3, 3' and 3").

A multiple channels feedback control unit 7 (e.g. N channel FGPA card) is used for achieving in parallel (a) monitoring transmembrane voltage through each of the TMDC thin layers, (b) monitoring the recording of the measurement of the ionic current in an electrical circuit (5, 5', 5") formed between a voltage source V (V', V") and electrodes 6a and 6b (6a", 6b"; 6a", 6b") immerged into the electrically conducting liquid on both sides of the corresponding TMDC thin layer 1, 1', 1" and (c) the turning off of the transmembrane voltage when a prescribed current/conductance is reached for the corresponding TMDC thin layer. The different thin layers (1, 1' and 1") can be provided in the form of thin membrane devices M1 to Mn mounted in parallel. A preamplifying unit for each of electrical circuit (6, 6', 6") can be connected to the multiple channels feedback control unit 7 and the voltage sources.

According to an embodiment, by for instance using a field programmable gate array (FPGA) board (NI PXI-7851R), the manufacture of a plurality of nanopores, for instance eight, can be monitored in parallel.

Moreover, a method according to the invention could also pave the way to cheaper sensing devices by taking advantage of wasteless in situ nanopore forming adapted for scale up production of 2D nanopores and shrink the costs for sensing devices based on such nanopore membranes.

Embodiments described herein may provide for improved methods and systems of forming nanopores and for detecting biological molecules in the nanopores. Embodiments include nanopores in solid state materials, which may allow for more consistent and easily fabricated structures. The solid state materials may allow for sub-nanometer or atomic level control of a nanopore formed within the materials. These nanopores may be fabricated in thin film materials, which when used to analyze a nucleic acid molecule, may allow only 1 to 3 bases in the nanopore at a time. This small number of bases may then increase the precision of detecting or analyzing biological molecules. Analyzing biological molecules may include single molecule nucleic acid sequencing. Furthermore, a thinner height of the material in which the nanopore is formed may facilitate wetting of the pores.

Embodiments may include a method of forming a nanopore having a desired diameter. The method may include applying a current having a constant amplitude and a constant frequency to a first liquid. The first liquid may be on one side of a layer of transition metal dichalcogenide crystals. The method may also include applying the current to a second liquid. The second electrically conductive liquid may be on another side of the layer of transition metal dichalcogenide crystals. Additionally, the method may include widening an aperture in the layer of transition metal dichalcogenide crystals until the nanopore having the desired diameter is formed.

In some embodiments, methods may include a method of forming a nanopore having a desired diameter. The method may include applying a voltage across a layer of transition metal dichalcogenide crystals. The layer of transition metal dichalcogenide crystals may have a first liquid on one side and a second liquid on another side. The method may also include widening an aperture in the layer of transition metal dichalcogenide crystals. The method may further include reducing the voltage to stop widening the aperture to form the nanopore having the desired diameter.

Embodiments may include a nanopore device for analyzing biological molecules. The nanopore device may include a layer of transition metal dichalcogenide crystals. The layer of transition metal dichalcogenide crystals may define an aperture. The nanopore device may also include an insulating material contacting the layer of transition metal dichalcogenide crystals. The device may further include a liquid on both sides of the layer of transition metal dichalcogenide crystals. In addition, the nanopore device may include two electrodes configured to apply a current to the liquid or a voltage across the electrodes. Both electrodes may be in the liquid. The components of the nanopore device may allow the nanopore device to detect and/or analyze biological molecules that enter the nanopore.

These and other embodiments may also include a device for analyzing biological molecules. The device may be created by any of the methods described herein.

Some embodiments may include a method of analyzing biological molecules. The method may include using any device described herein. The method may include translocation of a biological molecule through the nanopore. The biological molecule may be a biological polymer or a monomer derived therefrom.

Other features and advantages of the invention will be apparent from the claims, detailed description, and figures.

BRIEF DESCRIPTION OF THE DRAWINGS

FIG. 1A shows disposition of the 2D transition metal dichalcogenide for the in situ formation of a nanopore. FIG. 1B is a flowchart illustration of the steps of a process of the invention as implemented according to an exemplary embodiment of Example 1.

FIG. 2A is a schematic illustration of preparation of a freestanding $MoS_2$ membrane ready for electrochemical formation of a nanopore. In the center of the supporting 20 nm thick $SiN_x$ membrane a single focused ion beam, focused ion beam (FIB) hole is drilled to suspend a small portion of an intact monolayer $MoS_2$ flake. A single chip is mounted in the flow-cell for typical translocation experiments. A pair of electrodes (e.g. Ag/AgCl) is connected to a preamplifier is used to apply transmembrane voltage. FIG. 2B shows an optical image of the $SiN_x$ membrane with a FIB drilled hole in the center. FIG. 2C shows an optical image of the $SiN_x$ membrane with transferred triangular CVD-grown $MoS_2$ monolayer. FIG. 2D shows a low magnification TEM image of transferred CVD-grown $MoS_2$ monolayer covering the FIB hole. The FIB hole is indicated by the black arrow. FIG. 2E shows a high resolution TEM of the lattice of $MoS_2$ suspended over the FIB hole. The corresponding diffraction diagram is shown in the inset.

FIG. 3A shows a leakage current-voltage (I-V) characteristic of an intact $MoS_2$ membrane, for voltages below the critical voltage of 800 mV required for ECR which depends on the number of the membrane defects (more defects leads to higher current). FIG. 3B shows a representative ionic current trace measured for a $MoS_2$ membrane. Voltage is stepped by 100 mV with a 50 s holding, and the leakage current increases in accordance, being steady for a constant voltage. Sharp peaks at each voltage step originate from the capacitance charging. After a critical voltage, 800 mV is applied, the electrochemical reaction (ECR) starts (arrow), the current keeps increasing which triggers the feedback control to switch off voltage bias in order to halt the pore growth. FIG. 3C shows a mechanism of ECR based $MoS_2$ nanopore fabrication. A side view of the monolayer $MoS_2$ lattice, emphasizing the lattice having single atom (S) vacancy or defect before ECR V<Vcritical (left), $MoS_2$ lattice at V=Vcritical (nanopore starts to form, middle) and $MoS_2$ lattice when nanopore (diameter d) is formed (right). FIG. 3D shows a current-voltage (IV) characteristic of nanopores ranging in diameter from 1 to 20 nm—all nanopores are created via electrochemical reaction. Inset shows I-V characteristics for the system below and at the critical voltage. FIG. 3E shows TEM images verifying the nanopore formation and size (top being a zoom-in image of the bottom image).

FIG. 4A shows electric potential distribution in the trans chamber in the immediate vicinity of the membrane surface and (FIG. 4B) in the cis chamber. FIG. 4C shows electric potential distribution as a function of the distance from the pore. The applied potential was set to 800 mV and salt concentration was 1 M KCl. FIG. 4D shows typical current trace of nanopore formation on graphene membrane using ECR. A much higher transmembrane voltage, 2.8 V has to be applied to graphene to create a nanopore in graphene.

FIGS. 5A-E are schematization of nanopore forming in monolayer $MoS_2$ starting from a monolayer $MoS_2$ lattice. FIG. 5A is a top view of the monolayer $MoS_2$ lattice, the unit cell, u (parameter a=3.12 Å) is shown in grey (Hulliger, & Lévy. *Structural Chemistry of Layer-Type Phases, Springer*, 1976, p. 236). FIG. 5B shows ionic current-steplike features during the nanopore formation in FIG. 2A. FIG. 5C shows custom Matlab code is used to detect steps in the raw ionic current trace (Raillon et al., 2012, *Nanoscale*, 4, 4916-4924 and histogram of the trace shown in b) with corresponding color coded atom groups cleaved in each step during the pore formation from 1 to 21. FIG. 5D is an illustrative schematic of polygon removal corresponding to the histogram trace. Aberration corrected TEM micrograph of suspended single layer $MoS_2$ superimposed are the polygons which correspond to atom groups cleaved in the steps 1, 7, 14 and 21 during the pore formation. The coloring of atom groups cleaved in each step (FIG. 5C) and corresponding area polygons shown in the FIG. 5D starts from step 1 and goes up to step 21. In FIG. 5E, the table represents the sequence of cleaving $MoS_2$ unit cells and Mo and S atoms in 21 steps to form the pore. $I_{step}$ is the distance between two adjacent peaks in the current histogram; D and A are effective pore diameter and pore area, respectively; N is the number of unit cells equivalent to the effective area; ΔA is the increments of A; ΔN is the increments of N; ΔX is the nearest integer or integer +⅓ or +⅔ of ΔN; the last column on the right stands for the number of unit cells.

FIG. 6A is a typical trace of pNEB plasmid DNA translocation through an electrochemically etchhed nanopore recorded at 450 mV. The trace is downsampled to 10 kHz for display. FIG. 6B is a scatter plot of events collected at 300 mV and 450 mV bias. Event detection is performed using OpenNanopore37 Matlab code. Expectedly, the increase in the bias voltage from 300 to 450 mV shortens the translocation time and enhances the current drop.

FIG. 8 shows and example of arrangement of setting for carrying out the process of the invention for the in situ formation of a nanopore on several devices comprising a 2D transition metal dichalcogenide membrane in parallel through the control of an integrated circuit configured for the monitoring of the application and cut-off (e.g. N– channel FPGA card) transmembrane voltages in parallel to each of the 2D transition metal dichalcogenide membranes.

FIGS. 9A-C illustrate the process of the invention carried out on an exfoliated single layer of $WSe_2$. FIG. 9A shows an exfoliated single layer of $WSe_2$ transferred to silicon nitride membrane and positioned over the small opening on the same device layout as $MoS_2$ as described in Example 1. FIG. 9B shows current voltage characteristics of nanopore formed with ECR in $WSe_2$ when critical voltage of 1V reached. FIG. 9C is a representative ionic current trace measured for $WSe_2$ membrane for a voltage set to the critical voltage of 1V where the current keeps increasing until desired pore size is reached.

DETAILED DESCRIPTION OF THE INVENTION

Figure 1A:
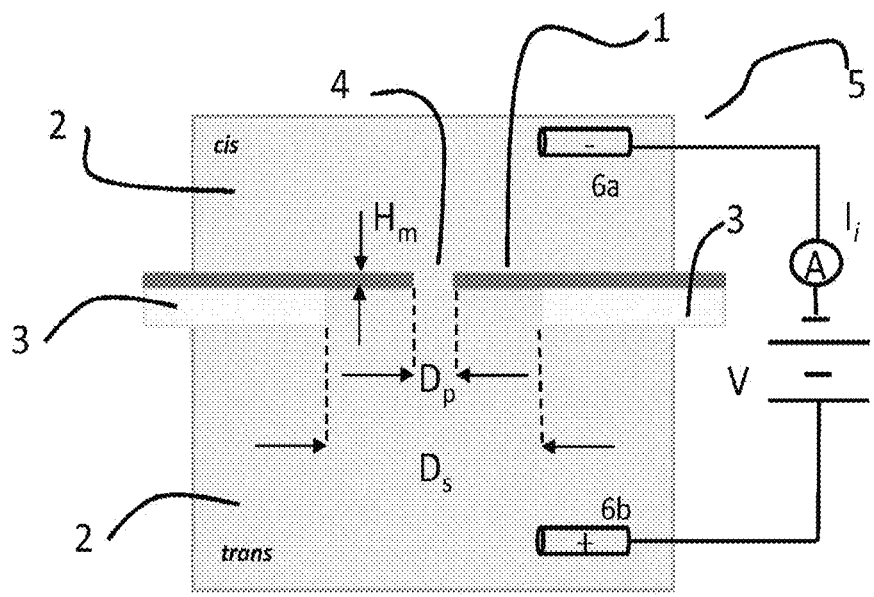
FIGS. 1A and 1B are illustrations of exemplary settings for carrying out the process of the invention.

Certain conventional methods of forming nanopores for detection or analysis of biological molecules may have certain disadvantages. Nanopores may be formed in protein layers, but protein layers may need to be inserted in a lipid bilayer. Lipid bilayers are often fragile, and methods of making nanopores in protein layers in lipid bilayers may have low yields. Additionally, the atomic and molecular moieties at the surface of a protein nanopore may not be known.

Some conventional solid state nanopores may present other problems. Extremely thin layers of materials such as silicon oxides and silicon nitrides may be difficult to deposit. These layers may be 5 to 10 nm in thickness, resulting in space for 50 to 100 bases in a single nanopore at the same time. Materials, such as silicon dioxide, may be prone to contamination from carbon and other compounds. Additionally, creating a nanopore with a target diameter may be difficult in these materials.

A material such as graphene may also not be ideal for forming nanopores. Graphene sheets are typically 1 Å thick, which may be too thin for detection or analysis of biological molecules. A biological molecule inside a graphene nanopore may not generate enough of a change in ionic current for accurate and precise detection or analysis. Graphene may also be conductive, which may generate interference when measuring current through the graphene.

Nanopores in a layer of transition metal dichalcogenide crystals may allow for improved fabrication and detection/analysis. Transition metal dichalcogenide crystals may not corrode easily. Additionally, a thin layer of transition metal dichalcogenide crystals may be formed, allowing for 1 to 3 bases to be in a nanopore at the same time. Furthermore, because the layer is crystalline, the atoms and chemistry at the surface of the nanopore and the rest of the layer is known. Conventional methods of forming nanopores often use a beam of ions or electrons, while methods described herein may not use such beams and instead use a pair of electrodes. Methods for forming nanopores and nanopore devices for detection or analyzing molecules are described herein.

Referring to the figures, in particular first to FIGS. 1A and 2A-E, a method for forming a nanopore in a transition metal dichalcogenide membrane, in a form of a thin layer (or a monolayer) 1 having from about 0.3 nm to 4 nm thickness ($H_m$) suspended in an electrically conducting liquid 2 comprises applying a transmembrane voltage (V) at a value higher than the oxidation potential of the transition metal of the said TMDC, measuring the ionic current ($I_i$) in the said electrically conducting liquid until the ionic current ($I_i$) has reached a value ($I_p$) corresponding to the electrical conductance of a pore within the metal dichalcogenide membrane having a prescribed diameter ($D_p$).

The TMDC thin layer 1 is configured such that the portion of the TMDC thin layer where the formation of a nanopore will be carried out is suspended in an electrically conducting liquid and the other portion of the TMDC thin layer is supported by a support layer 3.

The support layer can be of $SiN_x$, glass, quartz, $Al_2O_3$, or $HfO_2$ (or any other material that provides low capacitance membrane) with a support orifice of a diameter $D_s$ that allows the portion of the TDMC membrane where the pore formation should be conducted being suspended in the electrically conducting liquid.

When the transmembrane voltage V is applied to the TMDC thin layer at a value higher than the oxidation potential of the transition metal of the said TMDC, TMDC start being oxidized through an ECR reaction and the formation of a nanopore 4 is initiated.

The formation for a nanopore 4 could be monitored through the measurement of an increase in the ionic current ($I_i$) in an electrical circuit 5 formed between a voltage source V and electrodes 6a and 6b immerged into the electrically conducting liquid on both sides of the TMDC thin layer 1, and configured to measure the ionic current $I_i$ by a current measurement circuit portion A. The current measurement circuit portion A measures the ionic current value which is representative of conductance through the pore in the TMDC thin layer 1 and therefore of the diameter $D_p$ of the pore 4 formed in the TMDC thin layer 1.

Thin layers of $MoS_2$ with good quality suitable for use in a device according to the invention can be prepared by both exfoliation and chemical vapor deposition (CVD) (Novoselov et al., *PNAS*, 2005, 102, 10541-1053; Liu et al. 2012, *Nano Lett.*, 12, 1538-1544).

Typically, the thickness of TDMC membranes according to the invention can be assessed by Raman/optical electron microscopy, photo-luminescence (PL) measurements and Atomic Force Microscopy (AFM).

According to another particular aspect, the thickness of a TDMC membrane according to the invention may be less than 2 nm, typically from about 0.7 nm to less than 2 nm. In particular, the TDMC membrane is from about 0.7 nm (e.g. one layer) to about 1.4 nm thick (e.g. two layers).

According to another aspect, pores in the TDMC membrane formed by a process of the invention are nanometer sized, typically from about 1 nm to 20 nm diameter (for example typically from about 1 nm to about 5 nm, for example less than 4 nm or less such as about 3 nm) and from about 0.3 nm to 1 nm thickness (for example about 0.7 nm). Typically, the size of the pores can be measured by Transmission electron microscopy (TEM) and calculated from the current-voltage characteristics.

According to another aspect, the support layer can be a $SiN_x$, glass, or quartz (or any other material that provides low capacitance membrane) with a support orifice that allows the portion of the TDMC membrane where the pore formation should be conducted being suspended in the electrically conducting liquid. According to a further aspect, the support orifice has typically a diameter of from about 20 nm to about 500 nm (e.g. 50 nm), like for example from about 200 nm to about 500 nm and from about 20 nm to 50 nm thick.

According to a further aspect, the support layer can be coated with some curing layer such as polydimethylsiloxane (PDMS), while leaving the $MoS_2$ nanopore exposed in order to reduce the dielectric noise. Alternatively, support layer can be a quartz, glass, or any other material that provides low capacitance membrane based support.

According to a particular embodiment, the TDMC thin layer of the invention can be an active layer as described in WO 2012/093360.

According to a particular embodiment, the method of the invention can be carried out in a nanopore sensing device as generally described in PCT/EP2015/053042.

Referring to the method according to the invention, it has to be understood that the expression "turning off the transmembrane voltage" should be understood as encompassing the complete switching off the transmembrane voltage or alternatively the decrease of the transmembrane voltage to a value $V_d$ which is 50% of the voltage at which electrochemical reaction occurs for a given pore and experimental condition (pH, buffer composition, etc. . . . ) or lower than 50% of said voltage in order to stop the pore formation.

Figure 1B:
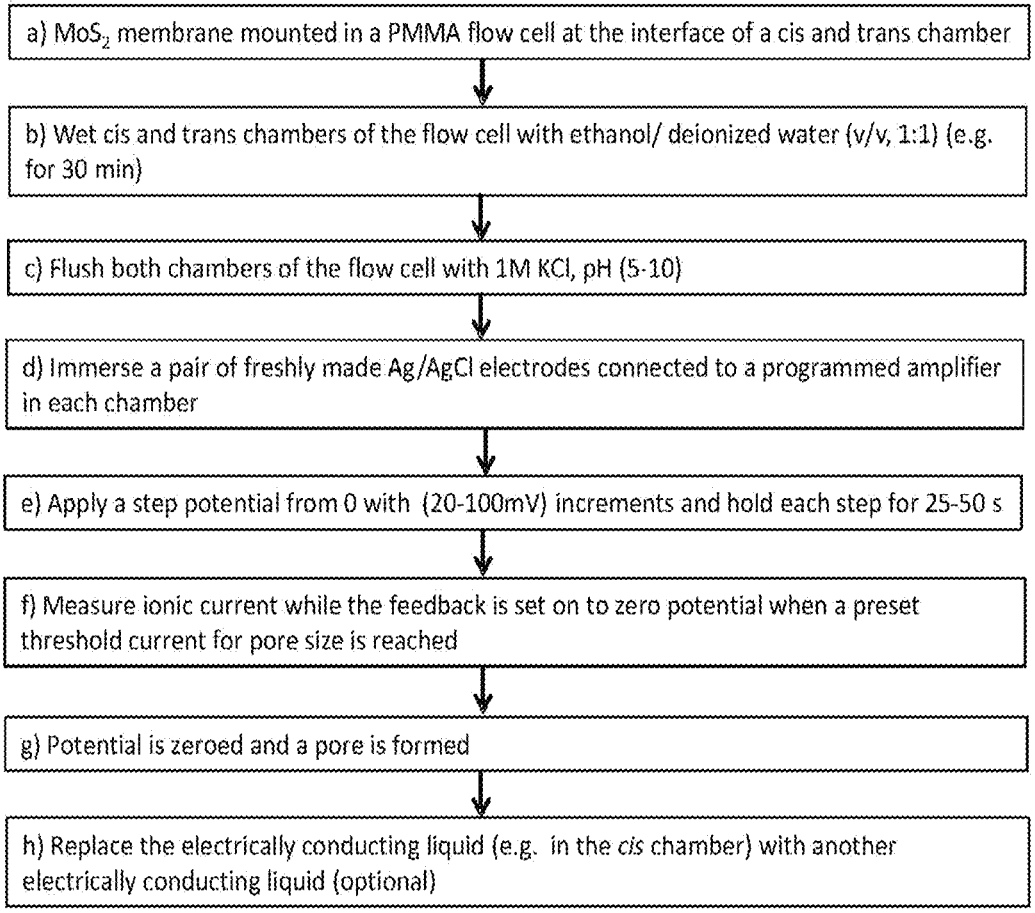

Referring to FIG. 1B, provided is an illustration of a specific embodiment regarding steps of a method for forming a nanopore in a transition metal dichalcogenide membrane according to the invention:
- (a) providing a TMDC thin layer mounted in a housing (e.g. polymethylmethacrylate (PMMA)) flow cell chamber on a support layer (e.g. $SiN_x$) with a support orifice that allows the portion of the TDMC membrane where the pore formation will be conducted being suspended in the electrically conducting liquid, wherein the housing comprises a cis and a trans chamber and the TMDC thin layer is located at the interface of those two chambers;
- (b) filling cis and trans chambers with an aqueous solution (e.g. a mixture of ethanol/deionized water v/v, 1:1) for increasing its hydrophilicity (e.g. for about 15-35 min);
- (c) flushing the cis and trans chambers with an electrically conducting liquid (e.g. 1M KCl) such as the TMDC thin layer is immersed in said electrically conducting liquid;
- (d) immersing a pair of electrodes adapted to the electrically conducting liquid (e.g. freshly made Ag/AgCl electrodes) in the corresponding chambers and connected to a voltage source, for example through a programmed amplifier;
- (e) applying a transmembrane voltage by step-wise increments (e.g. 20-100 mV increments) and holding each step for about 25-50 s;
- (f) measuring the ionic current ($I_i$) in the said electrically conducting liquid;
- (g) turning off the transmembrane voltage (i.e. by feedback control) once the measured ionic current ($I_i$) has reached a value ($I_p$) corresponding to the electrical conductance of a pore in the TMDC thin layer having a prescribed diameter ($d_p$).
- (h) optionally replacing the electrically conducting liquid in the cis chamber with another electrically conducting liquid (e.g. suitable for nanopore biosensing).

Apart from nanopore sensors, other applications for a method according to the invention can be envisioned such as water desalination devices such as described in Yuan & Gaoquan, 2014, *Nanoporous graphene materials, Materials Today*, 17 (2) 77-8 and Cohen-Tanugi D et al., 2012, 2012, Nano Letters, 12, p. 3602-3608.

The invention having been described, the following examples are presented by way of illustration, and not limitation.

EXAMPLES

Example 1: Preparation of $MoS_2$ Nanopores Using ECR

The present example illustrates a method of the invention applied to the fabrication of individual nanopores on single-layer MoS$_2$, with the electric field generated by Ag/AgCl electrodes located in two electrolytes compartments and positioned away from the membrane. As described below, the ECR process starts for a certain critical voltage applied to the membrane at a defect/vacancy present in the MoS$_2$ membrane.

Importantly, in the course of the ECR process, it is possible to control the successive removal of single or few MoS$_2$ units from the monolayer MoS$_2$ membranes. In this way, atom-by-atom nanopore engineering is achieved.

Figure 2A:
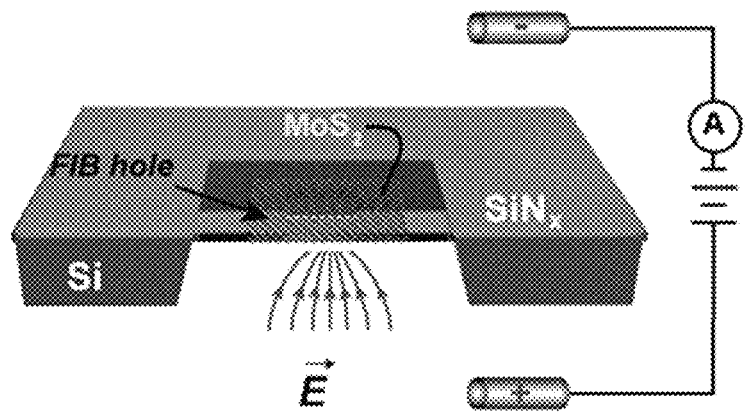
FIGS. 2A-E are illustrations of the use of a method of the invention for in situ fabricating nanopores in a transition metal dichalcogenide membrane in a molecular sensing system as described in Example 1.
Figure 2B:
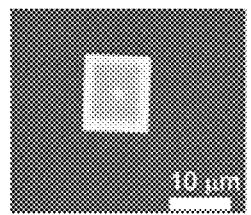
Figure 2C:
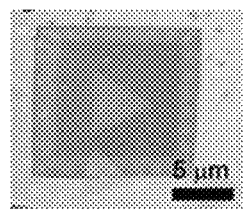
Figure 2D:
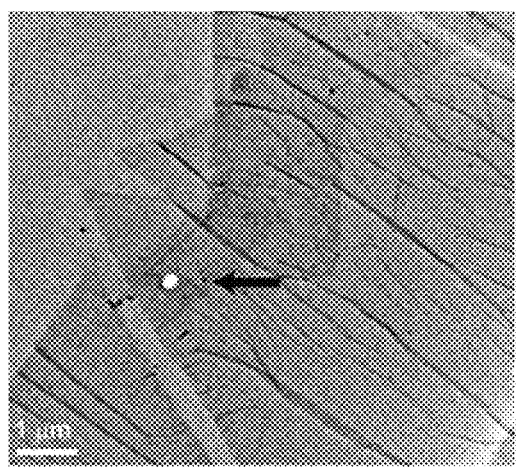
Figure 2E:
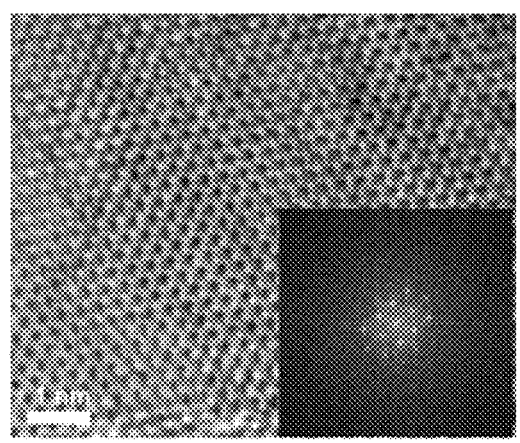

A procedure for fabricating MoS$_2$ nanopores using ECR is schematically illustrated in FIG. 2A, where two chambers (cis and trans) are filled with aqueous buffer (1M KCl, pH 7.4) and biased by a pair of Ag/AgCl electrodes which are separated by a single-layer MoS$_2$ membrane. Presence of an active site such as single-atom vacancy facilitates the removal of individual atoms and MoS$_2$ unit cells from MoS$_2$ lattice by ECR at voltages higher than the oxidation potential of MoS$_2$ in aqueous media. This process is facilitated by the electric field focusing by the pore itself. To form freestanding membranes, CVD-grown monolayer MoS$_2$ transferred from a sapphire substrate is suspended over focused ion beam (FIB) defined openings that ranged from 80 nm to 300 nm in diameter and were centered in a 20 nm thick SiN$_x$ membrane (FIG. 2B). A typical optical image of the transferred triangular flake of CVD-grown monolayer MoS$_2$ on the supporting silicon nitride membrane is shown in FIG. 2C. The freestanding MoS$_2$ membrane above the FIB defined opening can be further identified under TEM with low magnification (5 k×) as shown in FIG. 2D. MoS$_2$ flake is further characterized by Energy-dispersive X-ray spectroscopy (EDX) in TEM to reveal the chemical composition of the surface where elements of Mo and S are abundant in triangular areas. When moving to a high magnification (1 M×) and focusing on the freestanding portion of MoS$_2$ over the FIB opening, the atomic structure of MoS$_2$ can be clearly resolved as shown in FIG. 2E, and the diffractogram reflects the hexagonal symmetry of MoS$_2$, as shown in the inset of FIG. 2E.

Figure 3A:
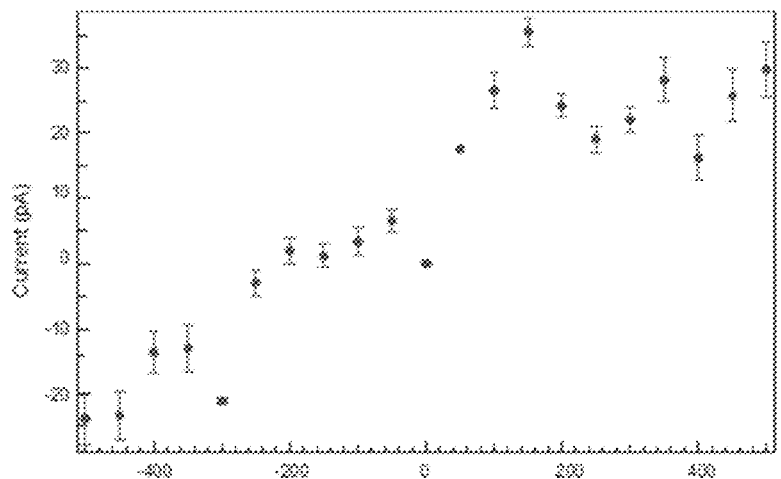
FIGS. 3A-E show the leakage current characteristics of an intact membrane and during pore formation as described in Example 1 together with the visualization and modelization of the pore forming process.
Figure 3B:
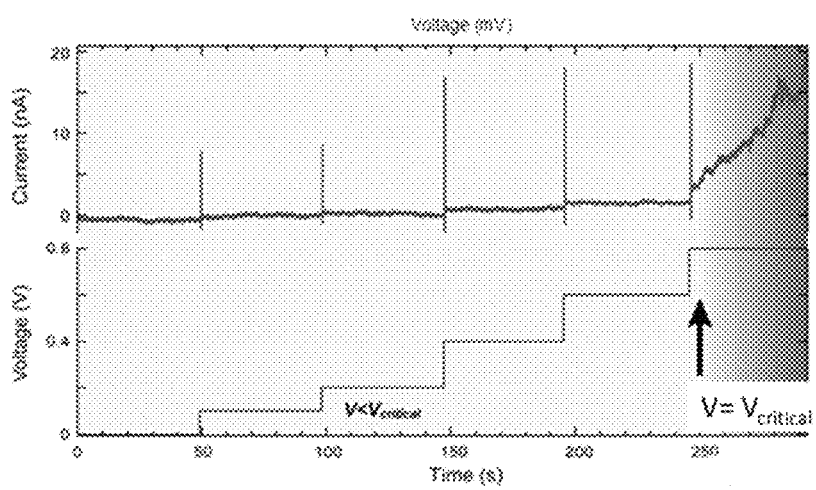
Figure 4A:
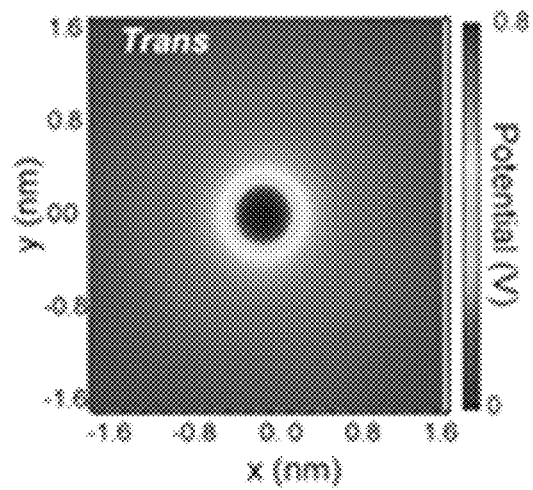
FIGS. 4A-D show simulations of the electric potential distribution for the nanopore in two dimensions for a freshly formed pore having a diameter of 0.3 nm and comparison with a typical current trace of nanopore formation on graphene membrane.

An intact MoS$_2$ membrane is mounted into a custom made microfluidic flow-cell filled with an aqueous buffer and transmembrane potential is applied using a pair of Ag/AgCl electrodes as shown in FIG. 2A. When a voltage is applied below the potential for electrochemical oxidation of the transition metal of the membrane, small leakage current is normally detected, typically on the order from tens to hundreds of picoamperes depending on the number of defects in the 2D membrane. As shown in FIG. 3A, the leakage current displays a non-ohmic characteristic. To reach the critical voltage value for achieving an ECR, the potential is gradually stepped, as shown in FIG. 3B. When the applied voltage is stepped up to 0.8 V (a critical voltage, indicated by the arrow), an increase of baseline current immediately occurs. This time-point indicates the nanopore creation which is associated to the electrochemical dissolution of MoS$_2$ enhanced by the electrical potential focused on the active site as shown in the potential profile obtained by the finite element analysis simulation (FIG. 4A). In other words, the pore growth continues at the initial, active site instead of another start on another defect because the pore itself focuses the applied electric potential and facilitates continuation of ECR on the active site where ECR process has already started.

In contrast to the avalanche-like dielectric breakdown process in silicon nitride, where a typically 10-minute waiting time for the filling of charge traps (Briggs et al., 2015, nanotechnology, 084004, doi: 10.1088/0957-4484/26/8/084004) under the application of critical voltage (>10 V) is needed before breakdown occurs, electrochemical dissolution happens spontaneously at the critical voltage.

Figure 3C:
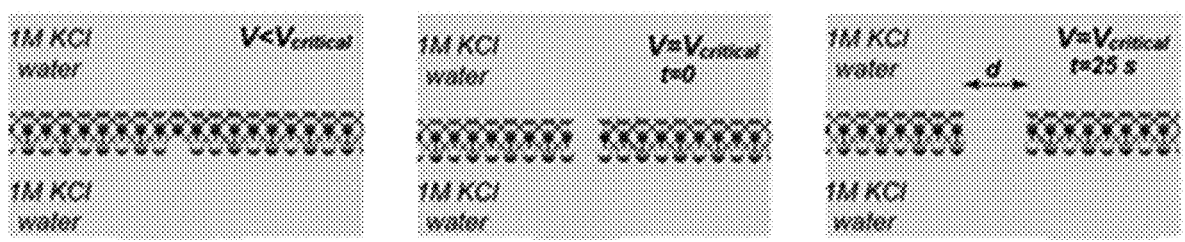
Figure 3D:
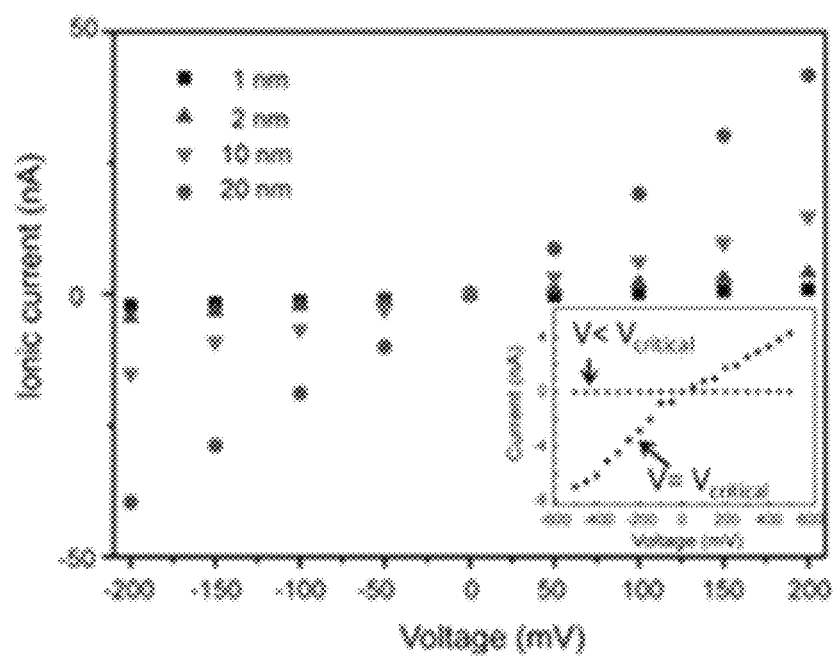
Figure 3E:
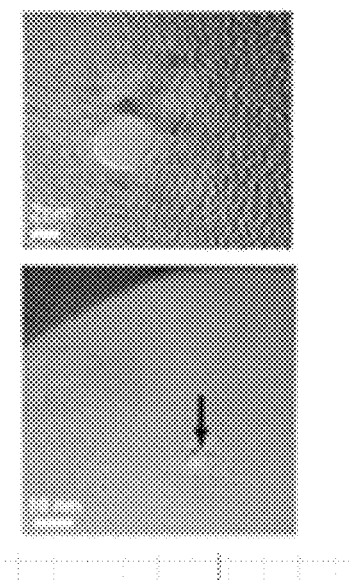

In addition, the observed rise of ionic current shows a quite slow rate (~0.4 nA/s). Therefore, it is possible to control the nanopore size by using an automatic feedback to cut off the voltage once the desired current/conductance threshold is reached. This feedback also helps to avoid multiple pore formation. Owing to the limited rates of electrochemical reaction, the MoS$_2$ nanopore sculpting process is quite slow, occurring on time scales of dozens of seconds to several minutes. FIG. 3E gives an example of ionic current trace to reach the threshold of 20 nA, for the critical voltage of 0.8 V.

Taking the advantage of existing theoretical insights to model the conductance-pore size relation (Kowalczyk et al., 2011, Nanotechnology, 22, doi:Artn 315101 Doi 10.1088/0957-4484/22/31/315101), the conductance of the nanopore (G) can be described by $$G = \sigma \left[ \frac{4L}{\pi d^2} + \frac{1}{d} \right]^{-1} \tag{1}$$

where σ, L and d are the ionic conductivity of solution, membrane thickness and nanopore diameter, respectively. Using this relation in combination with feedback on ECR that immediately stops the voltage once the desired pore conductance—that corresponds to a certain pore size—is reached, it is possible to fabricate pores ranging in diameter from 1-20 nm. FIG. 3E reveals current-voltage (I-V) characteristics of MoS$_2$ nanopores fabricated by ECR with different estimated sizes ranging from 1 nm to 20 nm. The symmetric and linear I-V curves also imply the well-defined shape of the fabricated pores. Similarly, as shown in the inset of the FIG. 3E, I-V characteristics across the membrane have been investigated in situ before and after ECR, confirming the pore formation.

To further verify the size of fabricated MoS2 nanopores, TEM has been used to image the newly formed nanopore. Exposure of 2D materials to electron radiation can induce large area damage and also open pores, as reported for both graphene (Fischbein et al., 2008, Applied Physics Letters, 93) and MoS2 (Liu et al., 2013, Nat. Commun., 4). Therefore, first aligned the beam was aligned on the suspended portion of MoS2 outside of the FIB opening and then quickly scanned the sample while taking care to minimally irradiate suspended MoS2 that houses ECR fabricated pore. FIG. 2C shows a TEM image of an ECR-fabricated MoS2 nanopore.

Figure 4B:
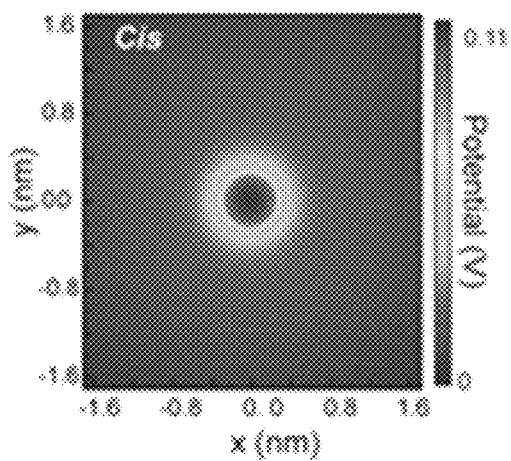
Figure 4C:
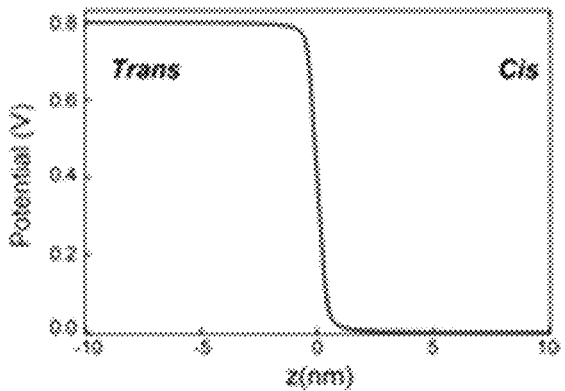
Figure 4D:
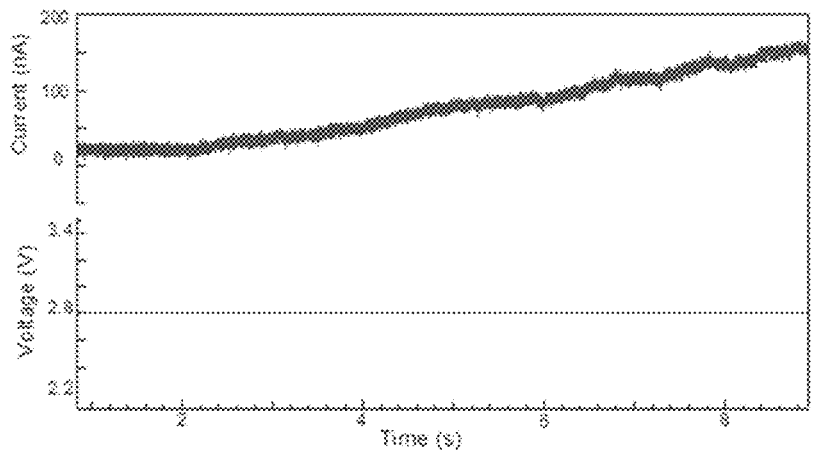

For the sake of comparison, a few graphene membranes (prepared as described below) have also been tested by this method and higher voltages (2-3V) are required to fabricate pores as presented in Supporting Information, with the typical ionic current trace is displayed in FIG. 4B.

The described ECR-based pore formation method benefits from the unique crystal structure of transition metal dichalcogenide (MX2) where atoms are situated in tree planes and linked by metal-chalcogenide bonds while in the case of graphene, carbon atoms are in the same plane and 3 bonds need to be removed to release one carbon atom. In addition, to remove carbon atoms, graphene needs to be oxidized to a higher valence state which presumably requires a higher voltage.

The physics of the electrochemically fabricated nanopores is determined by the focused electrical field and surface chemistries. The electric field concentrates at surface irregularities or defects which can be considered as surface active sites, and focuses current flow at the site of the pore, and thus locally enhances the electrochemical dissolution, as shown in FIG. 3C.

The surface dissolution chemistries can be understood as a surface bound oxidation scheme with hole capture and electron injection to produce the MoS2 oxidation state (Bonde et al., 2008, Faraday Discussions 140, 219-231) as shown in

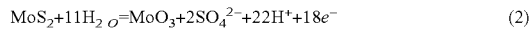

(2)

where $MoS_2$ is oxidized into $MoO_3$ which is water-soluble. Without being bound to any theory, this reaction is highly likely to happen considering the electrical potential (voltage bias) range applied to the membrane. Due to the current technical limitations of electron energy loss spectroscopy (EELS) analysis in the nanopore vicinity, it cannot be excluded the possibility that $MoS_2$ is oxidized to other valence states. Once an active site is removed by the process described above, indicating the initial formation of the pore, FIG. 5A, the electric field, as simulated in FIG. 4A, entirely focuses in this pore, which then prefers to enlarge the same pore since this is more energetically favorable than creating a second pore at another location. By applying at the beginning of the fabrication process a bias voltage higher than the critical voltage it might be possible to observe the formation of multiple pores. Given the stochastic nature of the pore creation process, with a configuration of voltage steps, multiple simultaneous nanoscale ECR events are highly unlikely. Furthermore, feedback control on the applied voltage to obtain the desirable conductance ensures the formation of a single nanopore. Finally, the formation of single nanopore is confirmed by TEM imaging.

Figure 5A:
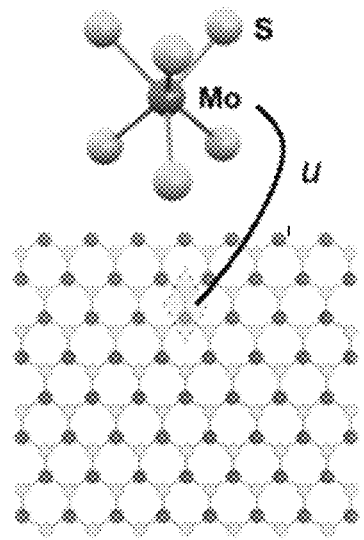

The advantage of an ECR-based nanopore fabrication technique of the invention, apart from the benefit of being a fast and cheap production lies in the possibility of fine-tuning the diameter of nanopores with unprecedented, single-atom precision. The low nanopore enlarging speed is due to low voltages and the electrochemical dissolution nature of the process. FIG. 5D is a 25-second long, continuous pore conductance trace that shows atomic precision during nanopore sculpting process. The trace starts from the critical point indicated in FIG. 3B. Fitting to the conductance-nanopore size relation, it can be estimated a pore diameter growth rate of about 1 angstrom per second. After 25 seconds a pore with a diameter 1.9*nm (area of 2.9 nm²) has been formed. The area of such a pore is equivalent to almost exactly N=34 unit cells of $MoS_2$ where the area of the unit cell u=0.0864 nm² (FIG. 5A). *The final pore size is 2.2, nm when one accounts for the initial 0.3 nm.

Figure 5B:
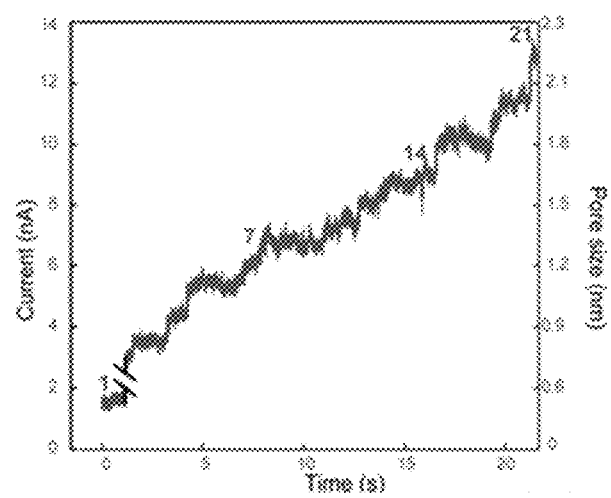

Surprisingly, the growth curve is not linear but step-like, as shown in FIG. 5B. Necessarily, the effective size of the pore enlarges with the same step-like characteristic. These step-like features are commonly observed when working with voltages around 1V. To gain insights into these step-like features, the histogram of current values is plotted from this trace in FIG. 5C, where 21 individual peaks can be extracted from the histogram.

Figure 5C:
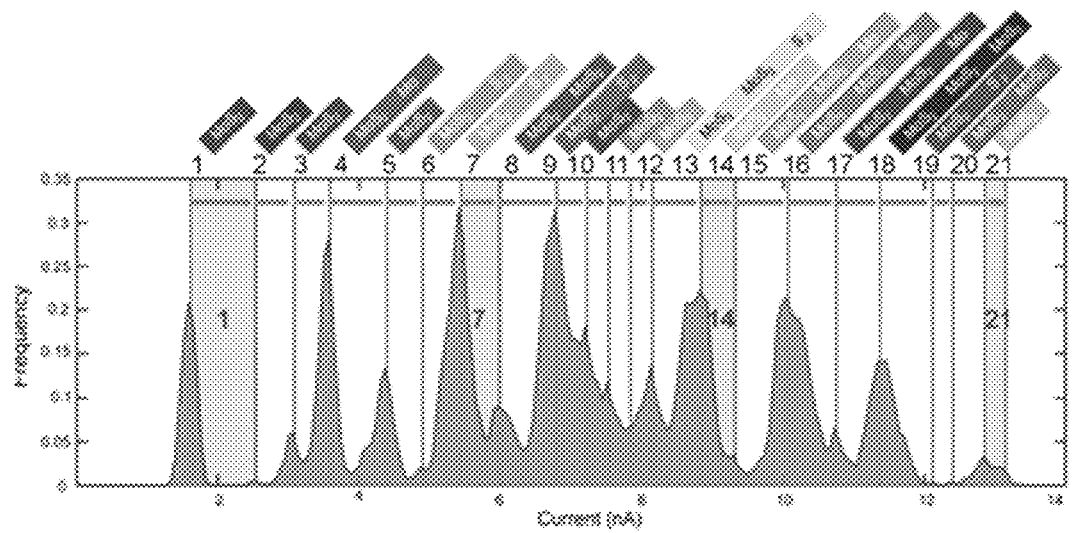
Figure 5D:
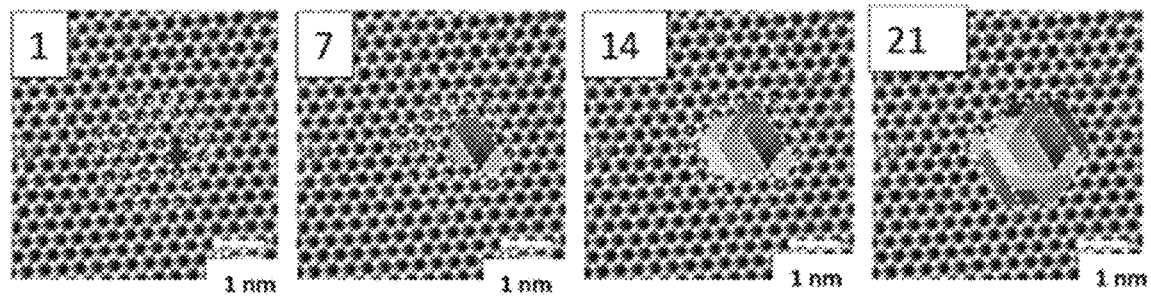

The sequence of the pore size enlargement steps may be normalized by the unit cell area u and a sequence of $MoS_2$ formula units and Mo and S atoms cleaved (corresponding to 21 current steps) to form the pore may be inferred, as presented in the FIGS. 5C and 5E. Several snapshots of the pore formation process taken at steps 1,7,14 and 21 are displayed in the FIG. 5D. The area of polygons corresponding to the cleaved atom groups follows the honeycomb structure of single-layer $MoS_2$, as presented in an aberration corrected TEM image FIG. 5D and in the schematics shown in FIG. 5A. The observed atomic steps here reveal the ultimate precision (single atoms) that can be reached in engineering nanostructures with a process of nanopore forming of the invention.

Membrane Set-Up

The $MoS_2$ membranes are prepared using the previously reported procedure (Liu et al., 2014, ACS Nano 8, 2504-2511) and as described below. Briefly, 20 nm thick supporting $SiN_x$ support membranes are manufactured using anisotropic KOH etching to obtain 10 μm×10 μm to 50 μm×50 μm membranes, with size depending on the size of the backside opening. Focused ion beam (FIB) is used to drill a 50-300 nm opening on that membrane. CVD-grown $MoS_2$ flakes were transferred from sapphire substrates using $MoS_2$ transfer stage in a manner similar to the widely used graphene transfer method and suspended on FIB opening (Dumcenco et al., 2015, ACS Nano., 9, 4611). Membranes are first imaged in the TEM with low magnification in order to check suspended $MoS_2$ flakes on FIB opening.

CVD $MoS_2$ Growth

Monolayer $MoS_2$ has been grown by chemical vapor deposition (CVD) on c-plane sapphire. After consecutive cleaning by acetone/isopropanol/DI-water the substrates were annealed for 1 h at 1000° C. in air. After that, they were placed face-down above a crucible containing ~5 mg $MoO_3$ (≥99.998% Alfa Aesar) and loaded into a furnace with a 32 mm outer diameter quartz tube. CVD growth was performed at atmospheric pressure using ultrahigh-purity argon as the carrier gas. A second crucible containing 350 mg of sulfur (≥99.99% purity, Sigma Aldrich) was located upstream from the growth substrates. Further details of the procedure are described in Dumcenco et al., 2014, supra.

CVD $MoS_2$ Transfer from Sapphire to $SiN_x$ Membrane

Monolayer $MoS_2$ grown on sapphire substrate (12 mm by 12 mm) is coated by A8 PMMA (495) and baked at 180° C. A diamond scriber was used to cut it into 4 pieces. Each piece is immersed into 30% w KOH at 85-90° C. for the detachment. Capillary force might be used in the interface between polymer and sapphire to facilitate the detachment and reduce the etching time in the KOH. The detached polymer film was repeatedly in DI water. Lastly, the "fishing" method of graphene transfer can be used to transfer CVD $MoS_2$ to the target $SiN_x$ membrane.

Nanopore Forming

For the nanopore fabrication experiments, after mounting in the polymethylmethacrylate (PMMA) chamber (FIG. 1B, step (a)), the chips were wetted with $H_2O$:ethanol (v:v, 1:1) for at least 20 min (FIG. 1B, step (b)). 1 M KCl solution buffered with 10 mM Tris-HCl and 1 mM EDTA at pH 8.0 was injected in the chamber (FIG. 1B, step (c)). A pair of chlorinated Ag/AgCl electrodes was immersed in the chamber (FIG. 1B, step (d)) and employed to apply the transmembrane voltage and the current between the two electrodes was measured by a FEMTO DLPCA-200 amplifier (FEMTO® Messtechnik GmbH). A low voltage (100 mV) was applied to check the current leakage of the membrane. If the leakage current was below 1 nA, the voltage bias was set up in 100 mV steps (25 s for each step) FIG. 1B, step (e)). At a critical voltage (i.e. 800 mV), the current started to immediately increase above the leakage level. A FPGA card and custom-made Lab View software was used for applying the voltage and monitoring the conductance (FIG. 1B, step (f)). The critical voltage was automatically shut-down by a feedback control implemented in LabView program as soon as the desirable conductance was reached (FIG. 1B, step (g)). Nanopores were further imaged using a JEOL 2200FS high-resolution transmission electron microscope (HR-TEM). STEM-EDX was performed on a ChemiSTEM-equipped FEI Tecnai Osiris transmission electron microscope (TEM). Aberration corrected TEM micrographs were taken on FEI Titan Themis.

CVD Graphene Growth for Comparative Examples

Large-area graphene films are grown on copper foils. The growth takes place under the flow of a methane/argon/hydrogen reaction gas mixture at a temperature of 1,000° C. At the end of the growth, the temperature is rapidly decreased and the gas flow turned off. The copper foils are then coated by PMMA and the copper etched away, resulting in a cm-scale graphene film ready to be transferred on the chips with membranes for fabricating nanopores with a method of the invention.

Finite Element Analysis Model

To estimate the potential drop in a defect in a $MoS_2$ membrane a finite element analysis was performed using COMSOL Multiphysics 4.4b. A coupled set of the Poisson-Nernst-Planck equations was solved in a 3D geometry with axial symmetry. In the modeled configuration cis and trans chambers were connected by a 0.3 nm pore in a 0.7 nm thick membrane suspended on a 50 nm wide and 20 nm thick hole. A 0.3 nm diameter defect can correspond to the absence of a unit cell of $MoS_2$. In the model, the applied potential was set to 800 mV and salt concentration was 1 M KCl. The minimal mesh size used was less than 0.2 Å.

Detailed Data Analysis of Ionic Current Steps Presented in FIGS. 5A-E

All analysis were implemented in Matlab R2014b. The raw signal was down-sampled to 5 kHz and then filtered using the edge-preserving Chung-Kennedy (CK) filter (Chung et al., 1991, *J. Neurosci. Methods*, 40, 71-86). The pore formation in 21 steps, presented on FIGS. 5A-E can be as follows: the growth of the nanopore is due to sequential cleaving of unit cells from $MoS_2$ lattice. The final pore area is 2.9 nm$^2$, which corresponds to 34 unit cells. Increments in the effective pore size $\Delta A$ are normalized by unit cell size $u=0.0864$ nm$^2$. The obtained number $\Delta N = \Delta A/u$ was rounded to the nearest integer, integer $+\frac{1}{3}$ or integer $+\frac{2}{3}$ to get $\Delta X$, the number of $MoS_2$ unit cells cleaved during the pore formation process. It is assumed that $\frac{1}{3}$ corresponds to a $S_2$ group and $\frac{2}{3}$ to a Mo atom, corresponding to the partial cleaving of a unit cell. It should be noted that the two S atoms in $MoS_2$ are stacked vertically and their combined surface area is smaller than that for Mo (which has about 50% larger radius).

The sequence of cleaving $MoS_2$ unit cells and Mo and S atoms in 21 steps to form the pore is given in the table from FIG. 5E. In order to depict the sequence of the pore formation, the numbering of the lines in this table and polygons based on HRTEM image starts from 1 to 21. Lifetime of the steps in the sequence is given in the same table. Initially irregular pore gradually becomes more symmetrical. The atom groups have been selected in the manner to minimize the number of dangling bonds at the edge of the pore. The pore formation sequence is not unique, however, the dangling bond constraint significantly reduces the number of pore formation scenarios and induces more symmetrical pore shape.

Example 2: DNA Sensing with Nanopores Fabricated by a Method of the Invention

Figure 6A:
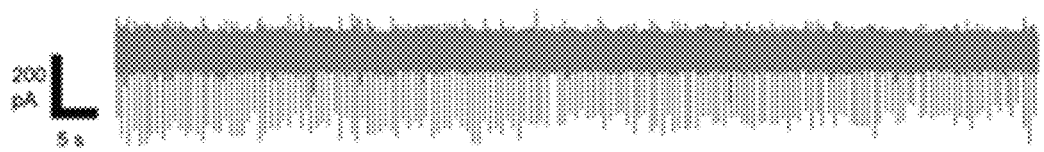
FIGS. 6A-B show DNA translocation through a nanopore fabricated as described in Example 1.
Figure 6B:
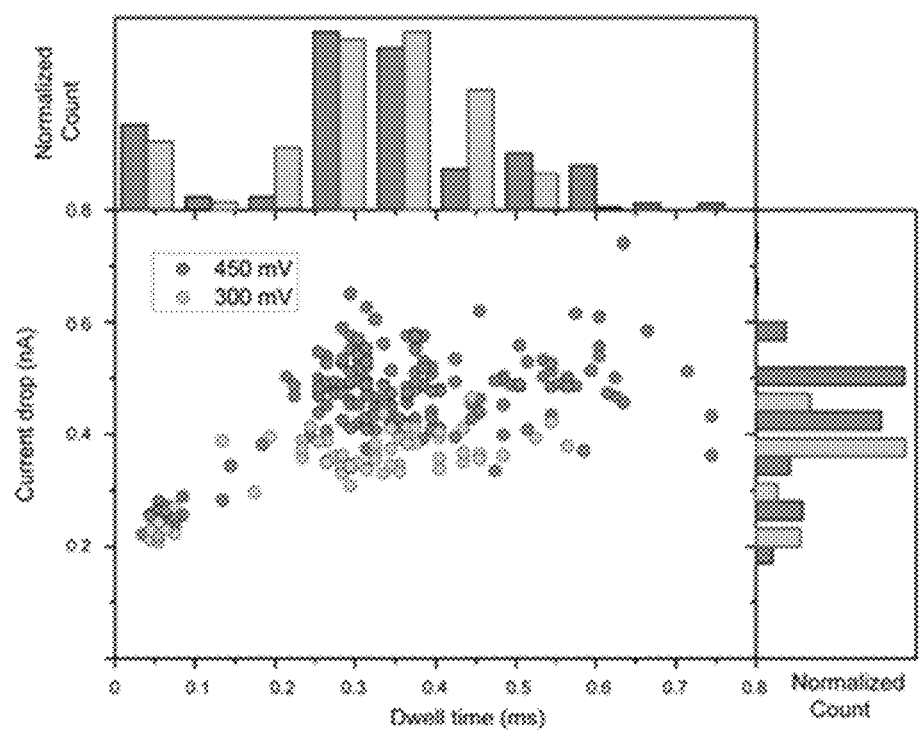
Figure 7:
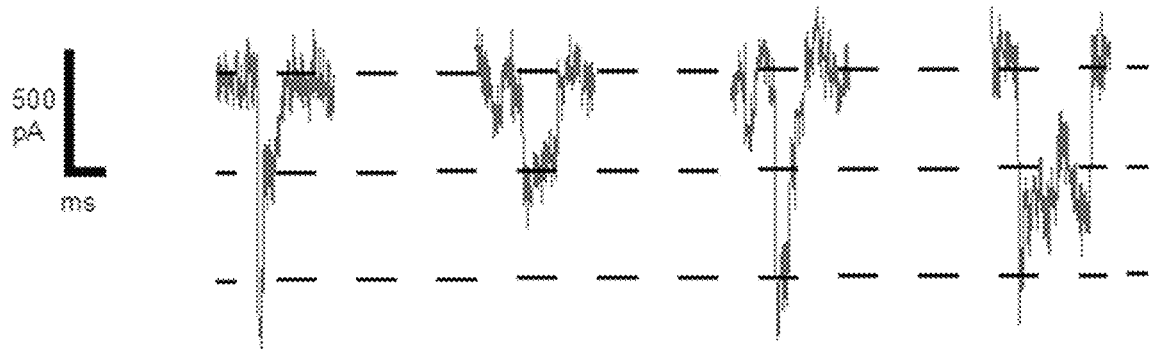
FIG. 7 shows selected events of λ-DNA translocation through a 4 nm ECR fabricated $MoS_2$ nanopore by a method according to the invention as described in Example 1 and recorded in-situ right after pore formation at 200 mV as described in Example 2. Quantized levels in the ionic current represent the flexibility of λ-DNA when translocating through nanopore.

To test the performance of ECR-fabricated pores, DNA translocation experiments were carried and detected the translocation events by the current drops below the baseline current. ECR fabricated $MoS_2$ nanopores consistently produces low-1/f noise on the current baseline in the range of 50-100 pA. The major contribution to the 1/f noise in 2D membrane nanopores can be attributed to mechanical fluctuations of the thin membranes. Higher frequency fluctuations are produced by the method itself. Fluctuation noise can be significantly reduced by using a smaller supporting opening, or operating at low temperatures. To show the ability of ECR fabricated nanopore for DNA detection, 2.7 kbp pNEB plasmid DNA (New England Biolabs) is translocated through a relatively large $MoS_2$ nanopore (25 nm) to eliminate the pore-DNA interaction and multiple conformation issues. FIG. 6A displays only one-level events indicating an extended (unfolded) DNA conformation, with SNR>10. Scatter plots are used to describe the statistics of DNA translocation as shown in FIG. 6B. The signal amplitude also increases linearly with the applied voltage, which is 0.5 nA for 450 mV and 0.38 nA for 300 mV as shown in the histogram FIG. 6B. Dwell times are also comparable with DNA translocation through a TEM-drilled $MoS_2$ nanopore of a similar diameter, for the same DNA and under same bias conditions. In addition, λ-DNA (48 k bp) is also translocated through an ECR-fabricated nanopore. As expected, folding scenario can be observed, manifested by quantization of current levels guided by dash lines. The upper dash line is the one level conductance, indicating a linear translocation. The bottom dash line is the two level conductance, indicating a folded translocation (FIG. 7).

Nanopore Testing for DNA Sensing

Current-voltage (I-V) characteristic and DNA translocation were recorded on an Axopatch 200B patch clamp amplifier (Molecular Devices, Inc. Sunnyvale, Calif.). DNA samples (pNEB193, plasmid 2.7 k bp, New England; λ-DNA, 48 k bp, New England) were diluted by mixing 10 μL of λ-DNA or pNEB stock solution with 490 μL 1 M KCl buffer. NI PXI-4461 card was used for data digitalization and custom-made LabView software for data acquisition using Axopatch 200B. The sampling rate is 100 kHz and a built-in low-pass filter at 10 kHz is used. Data analysis enabling event detection is performed offline using a custom open source Matlab code, named OpenNanopore (Raillon et al, *Nanoscale*, 2012, 4, 4916-4924) (lben.epfl.ch/page-79460-en.html).

Altogether, those data support that a method of the invention leads to reproducible and fully characterized nanopores by I-V characteristics and size as confirmed by TEM. Further, the intrinsic electrochemical reaction kinetics permits an advantageously high precision for nanopore fabrication at the atom level which can be monitored by the observed step-like features in the ionic current traces. Finally, the nanopores obtained through a method of the invention have demonstrated to allow DNA translocation and their sensing as fully functional nanopores.

Example 3: Preparation of WSe$_2$ Nanopores Using ECR

Figure 9C:
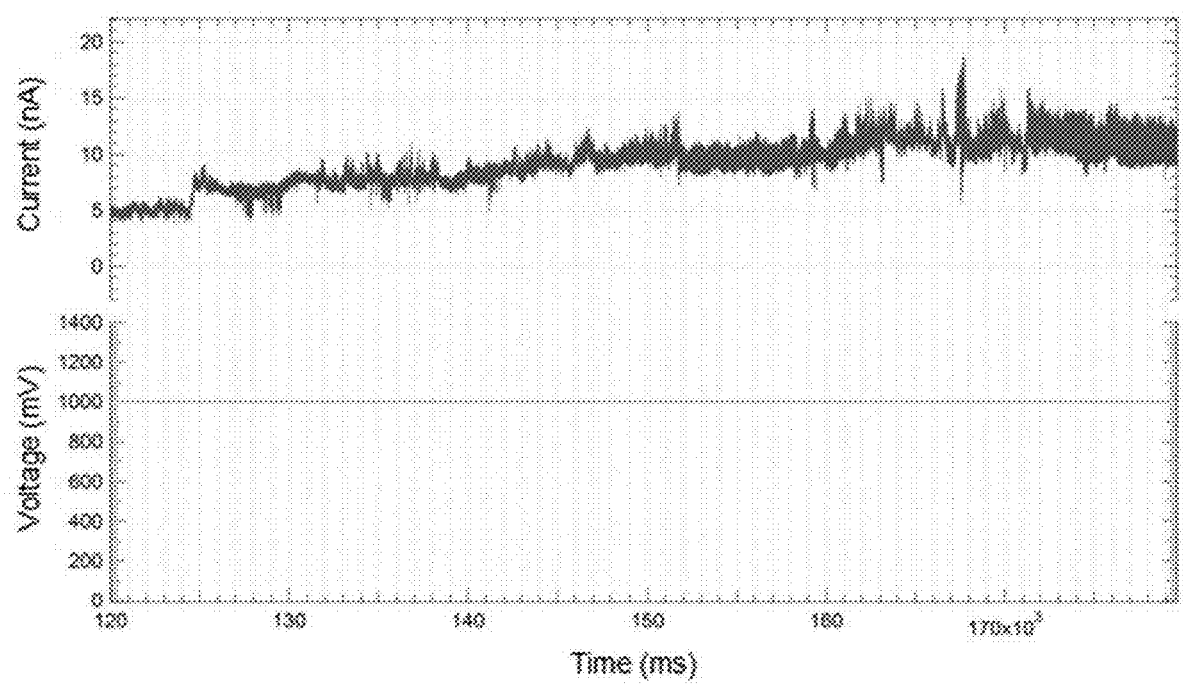

The present example illustrates a method of the invention applied to the fabrication of individual nanopores on single-layer of tungsten diselenide (WSe$_2$), with the electric field generated by Ag/AgCl electrodes located in two electrolytes compartments and positioned away from the membrane. Exfoliated single layer of WSe$_2$ has been transferred to silicon nitride membrane and positioned over the small opening on the same device layout as MoS$_2$ and as described in Example 1 (FIG. 9A)). This sample is mounted to the flow cell filled with 1M KCl (pH 11). Trans-membrane voltage is stepped gradually to reach critical voltage. A nanopore is formed at 1V and IV current voltage is taken immediately after pore formation and current voltage characteristics of nanopore formed with ECR in $WSe_2$ are similar to those of current voltage obtained with $MoS_2$ (FIG. 9B)) Representative ionic current trace measured for $WSe_2$ membrane. The corresponding ionic current trace measured for a voltage set to the critical voltage of 1V is represented under FIG. 9C) and the current keeps increasing until desired pore size is reached.

Constant Current Nanopore Formation

Apparatus for Controlling Current

In some embodiments, current may be held at a constant level in forming a nanopore of a given diameter, which may result in better control of the final diameter of the nanopore because the initial opening of an aperture significantly decreases the resistance in a circuit.

Figure 10A:
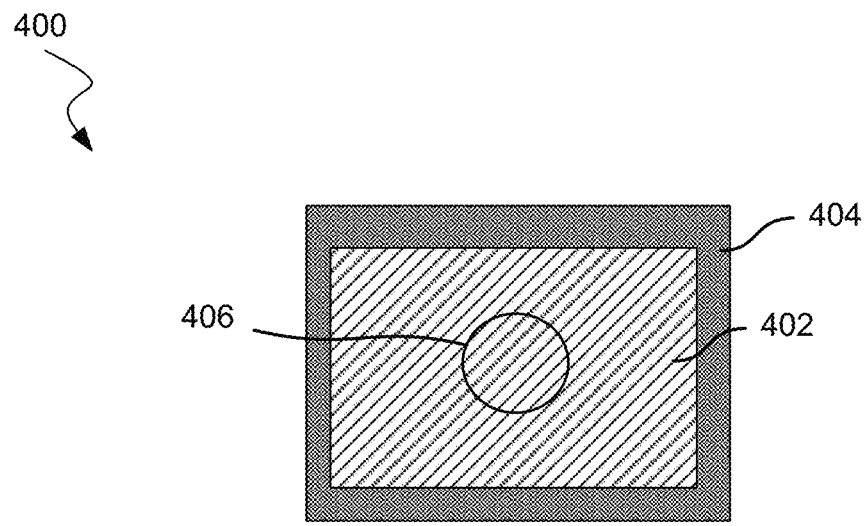
FIGS. 10A-D show an apparatus for forming a nanopore before and after an aperture is opened according to embodiments of the present invention.
Figure 10B:
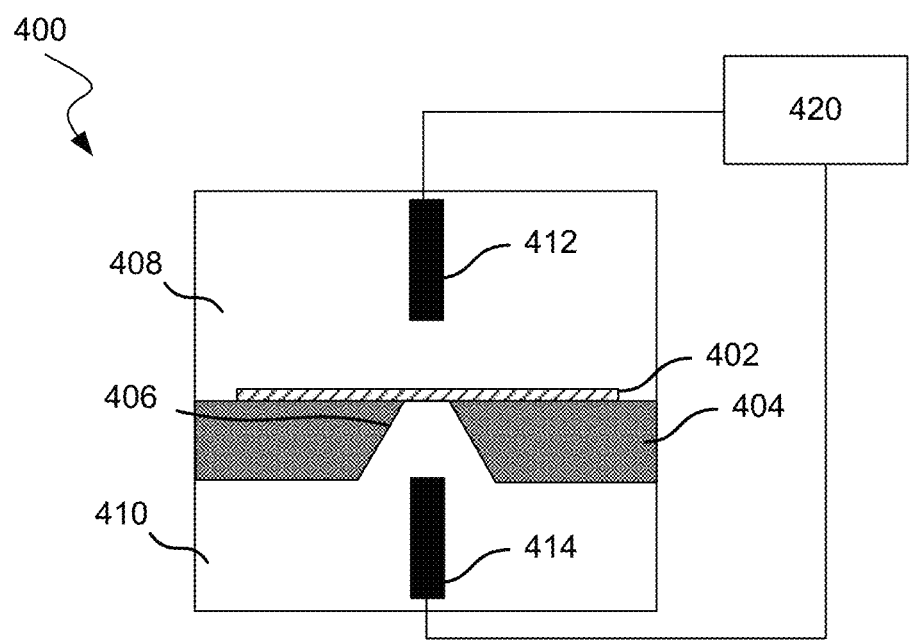

The apparatus for forming a nanopore before an aperture is defined is shown in FIGS. 10A and 10B. FIG. 10A shows a top view of apparatus 400 according to embodiments. FIG. 10B shows a side view of apparatus 400. These figures are not drawn to scale. A layer of transition metal dichalcogenide crystals 402 contacts insulating material 404. The insulating material may define an orifice 406. Orifice 406 may be patterned by e-beam and the reactive ion etching. Orifice 406 may have a diameter in a range from about 15 nm to about 80 nm. Orifice 406 may have sidewalls that are straight or tapered depending on the patterning technique.

On one side of layer of transition metal dichalcogenide crystals 402 may be a first liquid 408. First liquid 408 may be in a sealed compartment, such that no liquid can flow in or out of the sealed compartment. On the other side of layer of transition metal dichalcogenide crystals 402 may be a second liquid 410. Second electrically conductive liquid 410 may also be in a sealed compartment. First liquid 408 and second liquid 410 may be isolated from each other such that they are not in fluid communication, at least before the nanopore is formed. One electrode 412 may be in first liquid 408, and another electrode 414 may be in second liquid 410.

A power supply 420, also called a voltage source, can provide a voltage across electrodes 412 and 414. A circuit can be formed among wires connecting electrodes 412 and 414 and the power supply. The circuit may include other components, e.g., for a current measuring device for measuring current in the circuit, as will be known to one skilled in the art. A control circuit (not shown) may exist in power supply 420 or as a separate component for varying the voltage applied to the electrodes. For example, the control circuit can vary the voltage so that a current in the circuit is constant.

As a result of the voltage applied to electrodes 412 and 414, an aperture may be created in the layer of transition metal dichalcogenide crystals 402, and a current can flow between electrodes 412 and 414 through the first and second liquids. Each electrode may have a longitudinal axis. The longitudinal axis may be aligned with the length of the electrode and in the same direction as the length of the electrode. In some embodiments, the longitudinal axis may be a line about which the electrode is symmetric. For example, the longitudinal axis may be a line that bisects the electrode in the same direction as the length of the electrode. The longitudinal axis or a line coincident with the longitudinal axis may extend through orifice 406. At least one of the longitudinal axes of electrodes 412 and 414 may point toward orifice 406. A line having the shortest distance between electrode 412 and electrode 414 may pass through orifice 406 and/or an aperture that is formed later.

The current may flow from electrode 412 through first liquid 408, through layer of transition metal dichalcogenide crystals 402, through second liquid 410, and to electrode 414, or flow in an opposite direction. One electrode may be a ground electrode. Electrodes 412 and 414 may each be a few microns away from the layer of transition metal dichalcogenide crystals. As mentioned above, both electrodes 412 and 414 are in electrical communication with power supply 420, which may be configured to deliver at least one of a constant voltage or a constant current. The electrical circuit may include a control system for maintaining current at a constant level. The control system may include a processor.

Apparatus 400 may be one of a plurality of apparatuses for using nanopores to detect or analyze biological molecules. The plurality of apparatuses may include thousands to millions of apparatuses configured for multiplex analysis. The apparatuses may exist as an array of nanopores. A single ground electrode may exist, with each nanopore having a separate non-ground electrode.

Figure 10C:
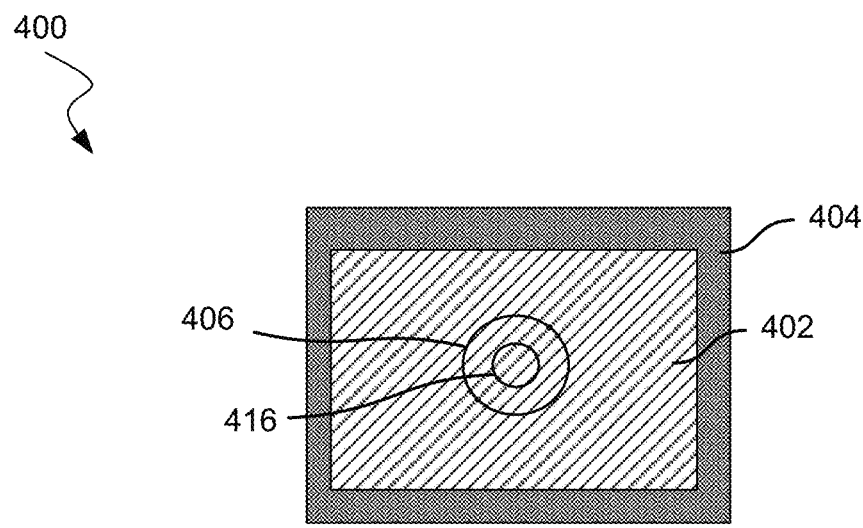
Figure 10D:
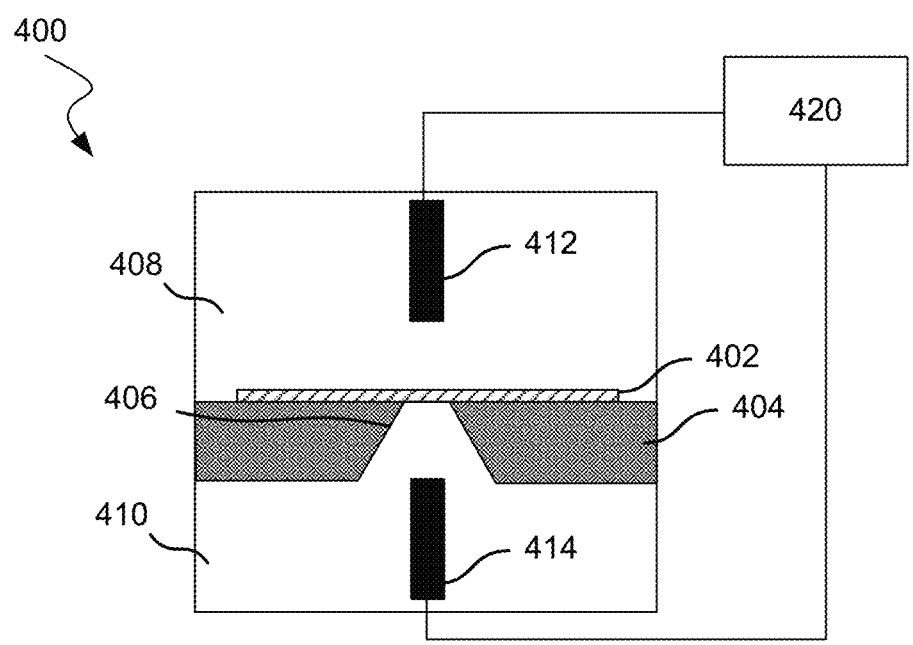

FIGS. 10C and 10D show the apparatus after an aperture has been defined. FIG. 10C shows a top view of apparatus 400, and FIG. 10D shows a side view of apparatus 400. An aperture 416 has formed in layer of transition metal dichalcogenide crystals 402. This aperture may be formed after a critical voltage is reached.

The formation of the aperture affects the current-voltage characteristics of the apparatus and may present certain advantages to maintaining a constant current. Voltage is related to current by Ohm's Law:

$$V=IR$$

where V is voltage, I is current, and R is resistance. Before an aperture is formed, the resistance of the circuit may be high. While liquids 408 and 410 may be conductive, layer of transition metal dichalcogenide crystals 402 may be a semiconductor. Once an aperture is formed, even if the diameter of the aperture is still small, an electrical path may pass through the electrically conductive liquid in the aperture, and the resistance of the circuit may decrease.

In scenarios where the voltage is increased gradually or stepwise, as shown in FIG. 3B, the current may be zero or near zero until the voltage reaches a critical voltage. At that critical voltage, an aperture forms. The resistance decreases with the opening of the aperture. If the voltage remains constant after the aperture forms, then the current increases and the aperture may continue to widen. The current may increase quickly, and the aperture may widen quickly. With such rapid increases in current, turning off the voltage at the exact moment the target diameter of the nanopore is reached may be difficult. As a result, the diameter of the nanopore may overshoot the target diameter.

In contrast, scenarios involving a current at a constant level throughout the formation of the aperture may result in improved control of the target diameter. Even before an aperture is formed, the voltage can be periodically adjusted to maintain current at a constant level (e.g., within a rated tolerance provided by the power supply). With no aperture, a large voltage may be generated. After the aperture is initially formed and the resistance decreases, the voltage may also decrease proportionally in order to maintain the current at a constant level. The current may be set at a level corresponding to the conductance of the electrically conductive liquids and a predetermined, target diameter of the nanopore. Once the diameter of the aperture matches the target diameter of the nanopore, the resistance and the voltage may remain constant, and the aperture may no longer widen. As a result, the voltage may not need to be decreased immediately when the target diameter is reached, and therefore, improved control in reaching the target diameter may be achieved. Indeed, both before and after the aperture is formed, the system may act to maintain the constant current by adjusting voltage. Because the control scheme remains largely the same, applying a constant current may also permit process simplicity and efficiency. Applying a constant current may involve different equipment than equipment used for applying a voltage with a variable current.

An aperture formed may be configured to have a subunit of a polymer molecule disposed within the aperture. A subunit of a polymer molecule disposed in the aperture may change a current between the first electrode and the second electrode. The change in current may be detectable, indicating the presence of the subunit of the polymer molecule.

Method

Figure 11:
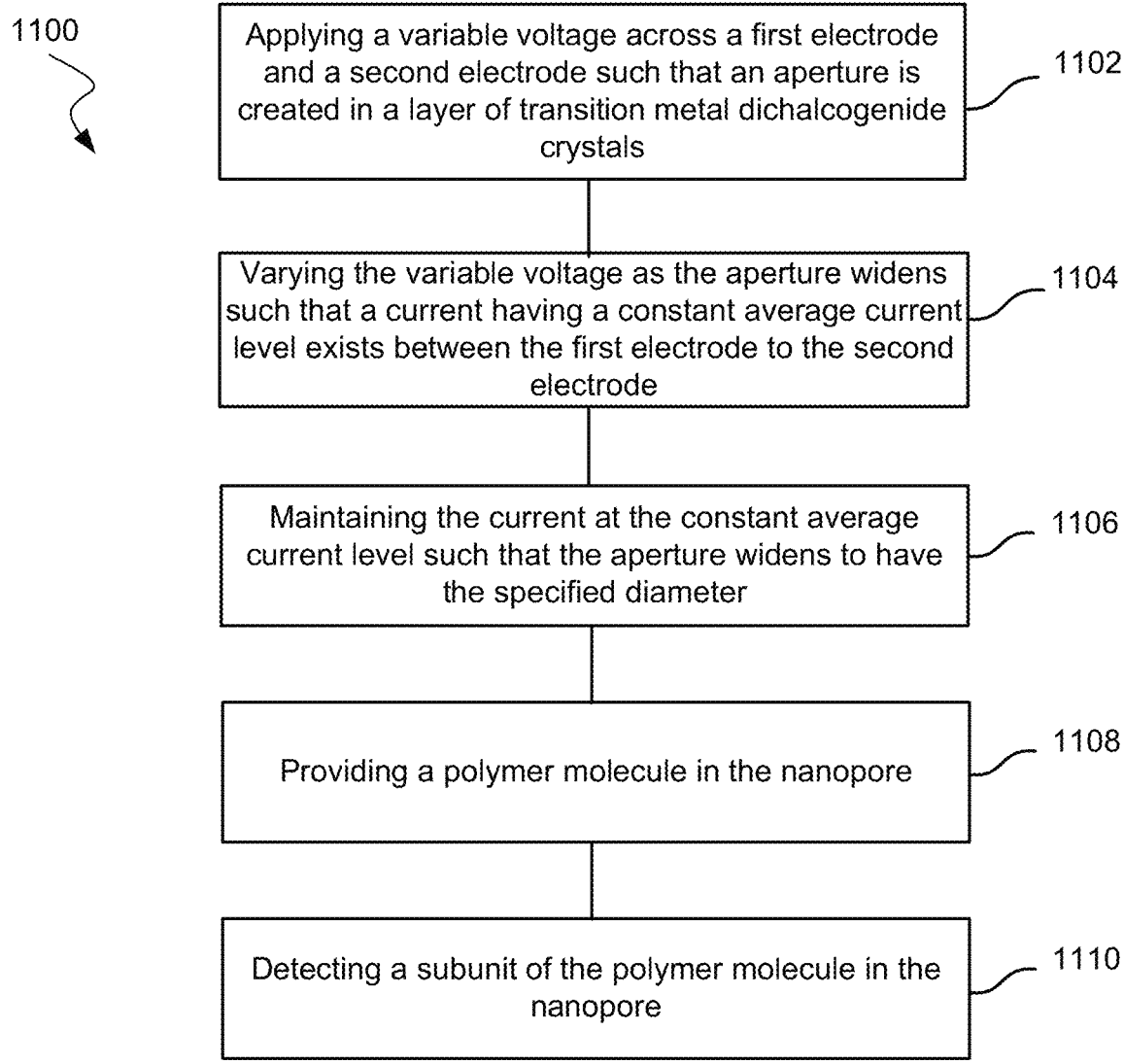
FIG. 11 shows a block flow diagram of a method of forming a nanopore using an applied variable voltage with constant current according to embodiments of the present invention.

As shown in FIG. 11, embodiments may include a method 1100 of forming a nanopore in a layer of transition metal dichalcogenide crystals.

At block 1102, a variable voltage may be applied across a first electrode and a second electrode such that an aperture is created in the layer of transition metal dichalcogenide crystals. The layer of transition metal dichalcogenide crystals may be between a first electrode and a second electrode, with the first electrode on one side of the layer and the second electrode on another side of the layer. For example, the first electrode may be on an opposite side of the layer as the second electrode.

A first liquid may be on one side of the layer of transition metal dichalcogenide crystals, and a second liquid may be on another side of the layer of transition metal dichalcogenide crystals. The first liquid may include aqueous, organic, or ionic liquid and may be electrically conductive. The first liquid may include ions formed from a salt. The salt may be an inorganic salt and may include one selected from the group consisting of KCl, LiCl, NaCl, and $MgCl_2$. In addition, the first electrically conductive liquid may include a room temperature ionic liquid (RTIL). The second liquid may be any of the liquids listed for the first liquid. In some embodiments, the second liquid may have a same or different composition from the first liquid.

The transition metal dichalcogenide crystals may include a compound having a chemical formula $MX_2$, where M is a transition metal atom, and X is selected from the group consisting of sulfur, selenium, and tellurium. Transition metal atoms may include Ta, Nb, Mo, W, Ti, and Re. The transition metal dichalcogenide crystals may include a compound selected from the group consisting of $MoS_2$, $SnSe_2$, $WS_2$, $TeS_2$, $MoSe_2$, $WSe_2$, $TeSe_2$, $NbS_2$, $NbSe_2$, $TiS_2$, $TiSe_2$, $ReS_2$, and $ReSe_2$.

The layer may be one monolayer thick, two monolayers thick, or three monolayers or more thick. The thickness of the layer may range from about 0.3 nm to about 5 nm. A monolayer may include the transition metal atom sandwiched by two planes of chalcogenide crystals. For example, as shown in FIG. 5A, a molybdenum atom may be between two planes of sulfur atoms. Based on this structure, the layer may be three atoms thick. The crystalline structure of the layer may allow for predictable or quantifiable effects at the edges of the layer, where a nanopore is later formed.

The layer of transition metal dichalcogenide crystals may be contacting an insulating material. The insulating material may include silicon nitride, glass, $Al_2O_3$, $HfO_2$, quartz, or $TiO_2$. The insulating material may define an orifice.

The aperture may form within the orifice defined by the insulating material. In other words, a line going through the center of the orifice and orthogonal to the insulating material may extend through the aperture.

At block 1104, method 1100 may include varying the variable voltage as the aperture widens such that a current having the constant average current level exists between the first electrode to the second electrode. The current may be an alternating current or a direct current. Direct current may be considered to have zero amplitude and zero frequency. The current may have a constant average current level corresponding to a specified diameter of the aperture to be formed. The resistance of the circuit may drop as the aperture forms. The current may be maintained at a constant average current level by adjusting the variable voltage. The formation of the aperture may be detected by measuring a drop in the variable voltage. As examples, the average current level for an alternating current may be defined as the average current for one cycle or as a root mean square average. With alternating current, a constant average current level can result from a constant amplitude for the current. The current applied may be in the fA, pA, nA, µA, mA, or A range.

At block 1106, method 1100 may include maintaining the current at the constant average current level such that the aperture widens to the specified diameter. After the aperture forms, the current may exist through the aperture instead of through the layer of transition metal dichalcogenide crystals. In some embodiments, the aperture may continue to widen past the specified diameter even if average current level is not increased, but the aperture may have the specified diameter at some given time. In some embodiments, chemical entities may be added to the liquids on either one or both sides to react with the molecular entities constituting the edge of the layer of transition metal dichalcogenide crystals defining the widening aperture.

Method 1100 may further include decreasing the variable voltage to maintain the current at the constant average current level after the aperture having the specified diameter is formed. Analysis of the voltage, resistance, or the duration of current applied may help indicate when the specified diameter is reached. After the specified diameter is reached, the current may no longer be maintained at a constant average current level. The current may be decreased by decreasing the voltage. Decreasing the voltage may include decreasing the voltage to 0 V. Decreasing the voltage may include turning off the voltage as rapidly as possible. Decreasing the voltage may include decreasing the voltage to a level suitable for detection or analysis of a polymer molecule (e.g., when the polymer molecule is in linear form) in the nanopore. In some embodiments, method 1100 may include maintain voltage at a constant level after the aperture having the specified diameter is formed.

At block 1108, method 1100 may further include providing a polymer molecule in the nanopore. The polymer molecule may be introduced into the first or second liquid. Method 1100 may also include applying a voltage across the two electrodes and/or may include providing a current between the two electrodes.

At block 1110, method 1100 may further include detecting a subunit of a polymer molecule in the nanopore. The charged electrodes may drive anions in the solution to the positive electrode and cations in the solution to the negative electrode, creating an ionic current. If a subunit of a polymer molecule enters the nanopore, it may disrupt the ionic flow. The subunits of the polymer molecule may be detected by measuring a change in the ionic current. Polymer molecules may include DNA, single-stranded DNA, RNA, proteins, and non-native polymers. Non-native polymers may include a molecule such as DNA with an artificial tag inserted in the molecule to make the molecule easier to be detected or analyzed by the nanopore. As examples, the subunit of the polymer molecule may include a base or a plurality of bases for nucleic acids or amino acid(s) for proteins. Different subunits may have different effects (e.g., amplitude and dwell time) on the current, and as a result, different subunits may be identified.

The liquids, layer of transition metal dichalcogenide crystals, voltage, current, aperture, nanopore, and electrodes may be any described herein.

Applied Voltage with Variable Current Nanopore Formation Method

Figure 12:
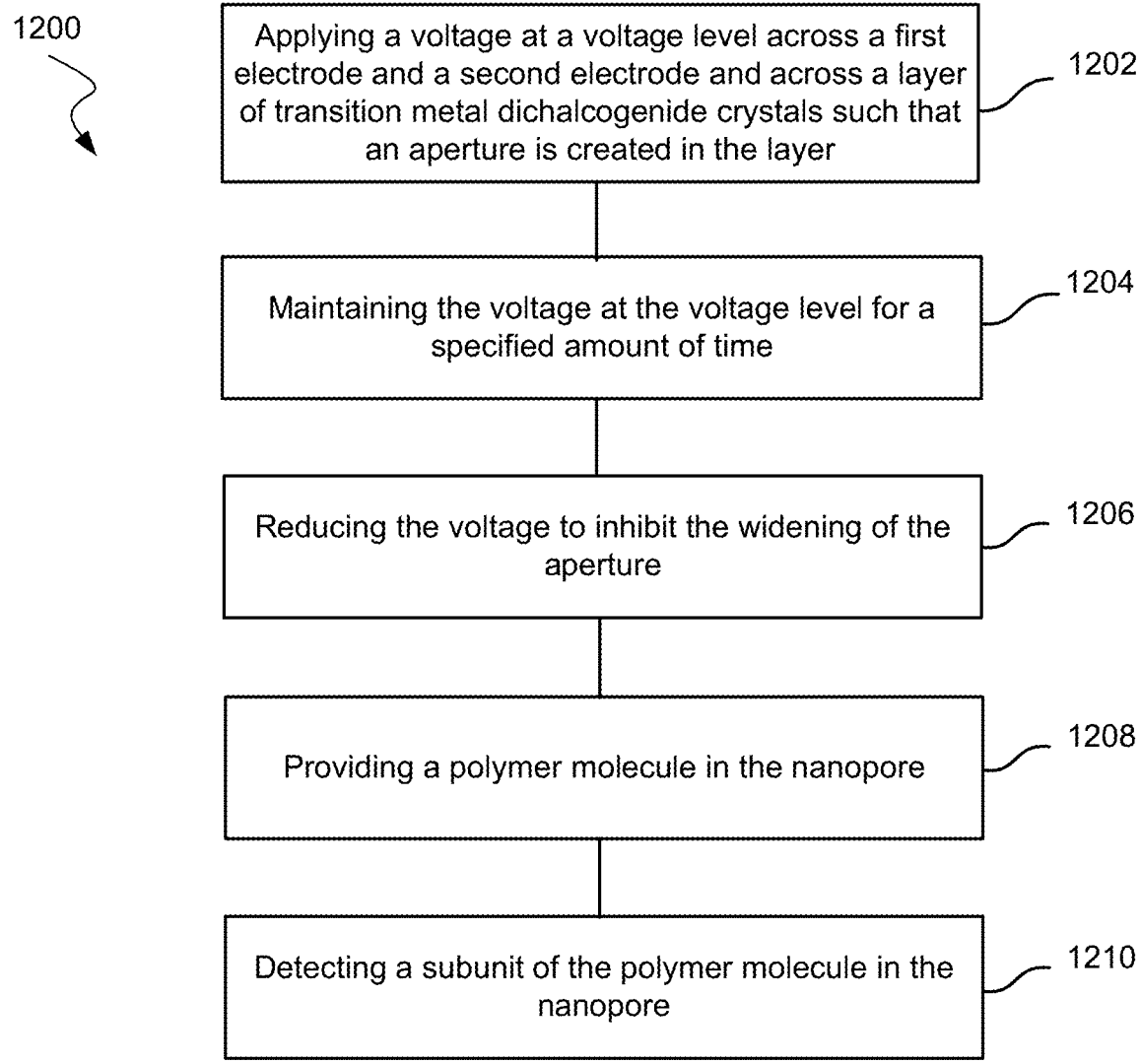
FIG. 12 shows a block flow diagram of a method of forming a nanopore using an applied voltage with variable current according to embodiments of the present invention.

As shown in FIG. 12, embodiments may include a method 1200 of forming a nanopore in a layer of transition metal dichalcogenide crystals.

At block 1202, a voltage at a first voltage level may be applied across a first electrode and a second electrode and across the layer of transition metal dichalcogenide crystals such that an aperture is created in the layer of transition metal dichalcogenide crystals. Previous to the first voltage level being achieved, the voltage may be applied in a stepwise or increasing manner until the voltage reaches the first voltage level corresponding to the formation of the aperture. The first voltage level may be higher than the oxidation potential of the transition metal of the transition metal dichalcogenide crystals. The voltage may be at a level in a range from about 800 mV to 1,000 mV. The voltage may include a direct current voltage or an alternating current voltage.

At block 1204, the voltage may be maintained at the first voltage level for a specified amount of time. The specified amount of time may correspond to the aperture widening to have at least a specified diameter. As examples, the specified amount of time may be determined by measuring the time to achieve a given average current, or the specified amount of time may be based on average times for apertures to be created with the specified diameter in previous samples. When previous samples are used, the amount of time can be determined from a statistical distribution of the times (e.g., as determined by measuring current) to create the nanopores with the specified diameter. The amount of time to use can be based on various statistical parameters of the statistical distribution, e.g., the time can be taken as the average, mode, median, specific percentiles (e.g., 90% of nanopores have at least the specified diameter at the given amount of time), or standard deviations.

At block 1206, the voltage may be reduced to a second voltage level to inhibit the widening of the aperture. Method 1200 may include measuring a current through the first liquid and the second liquid. The current may be reduced after the current reaches an average current level corresponding to the specified diameter of the aperture. Reducing the voltage may include activating a switch through a feedback control circuit when the current level is reached. The aperture may continue to widen past the specified diameter even after the voltage is reduced. However, the aperture may eventually stop widening and reach a maximum diameter. The second voltage level may be non-zero.

At block 1208, method 1200 may include providing a polymer molecule in the nanopore. The polymer molecule may be provided similar to other methods described herein.

At block, 1210, a subunit of the polymer molecule in the nanopore may be detected, similar to other detection methods described herein.

The liquids, layer of transition metal dichalcogenide crystals, voltage, current, aperture, nanopore, and electrodes may be any described herein.

What is claimed is:

1. A method of forming a nanopore in a layer of transition metal dichalcogenide crystals residing between a first electrode on a first side of the layer of transition metal dichalcogenide crystals and a second electrode on a second side of the layer of transition metal dichalcogenide crystals, wherein a first liquid is disposed on the first side and a second liquid is disposed on the second side, the method comprising:
   applying a voltage at a first voltage level across the first electrode and the second electrode and across the layer of transition metal dichalcogenide crystals such that an aperture is created in the layer of transition metal dichalcogenide crystals, wherein the applying the voltage comprises applying a direct current voltage; and
   maintaining the voltage at the first voltage level for a specified amount of time, the specified amount of time corresponding to the aperture widening to have at least a specified diameter;
   after the specified amount of time, reducing the applied voltage to a second voltage level to inhibit the widening of the aperture.

2. The method of claim 1, wherein:
   the transition metal of the transition metal dichalcogenide crystals has an oxidation potential, and
   the first voltage level is higher than the oxidation potential.

3. The method of claim 1, further comprising measuring a current between the first electrode and the second electrode, and
   wherein reducing the applied voltage comprises reducing the applied voltage after the current reaches a current level corresponding to the specified diameter of the aperture.

4. The method of claim 3, wherein reducing the voltage comprises activating a switch through a feedback control circuit when the current level is reached.

5. The method of claim 4, wherein the activation of the switch turns off the applied voltage.

6. The method of claim 1, wherein the first voltage level is in a range from 800 mV to 1,000 mV.

7. The method of claim 1, wherein the transition metal dichalcogenide crystals comprise a compound having a chemical formula $MX_2$, wherein M is a transition metal atom, and wherein X is selected from a group consisting of sulfur, selenium, and tellurium.

8. The method of claim 1, wherein the transition metal dichalcogenide crystals comprises a compound selected from the group consisting of $MoS_2$, $SnSe_2$, $WS_2$, $TeS_2$, $MoSe_2$, $WSe_2$, $TeSe_2$ $NbS_2$, $NbSe_2$, $TiS_2$, $TiSe_2$, $ReS_2$, and $ReSe_2$.

9. The method of claim 1, wherein the layer of transition metal dichalcogenide crystals is disposed on an insulating material.

10. The method of claim 1, wherein:
    the first electrode is disposed in the first liquid, and
    the second electrode is disposed in the second liquid.

11. The method of claim 1, wherein the layer of transition metal dichalcogenide crystals has a thickness in a range from 0.3 nm to 5 nm.

12. The method of claim 1, wherein the layer of transition metal dichalcogenide crystals is one monolayer thick.

13. The method of claim 1, wherein the layer of transition metal dichalcogenide crystals is two monolayers thick.

14. The method of claim 1, wherein the specified diameter is in a range from 1 nm to 5 nm.

15. The method of claim 1, further comprising detecting a subunit of a polymer molecule in the nanopore based on electrical signals detected by at least one of the first electrode and the second electrode.

16. The method of claim 1, wherein the specified amount of time is based on average times for apertures to be created with the specified diameter in previous samples.

* * * * *